US009122430B1

(12) United States Patent
Tedesco et al.

(10) Patent No.: US 9,122,430 B1
(45) Date of Patent: *Sep. 1, 2015

(54) PORTABLE PROMPTING AID FOR THE DEVELOPMENTALLY DISABLED

(71) Applicant: HandHold Adaptive, LLC, Shelton, CT (US)

(72) Inventors: Daniel E. Tedesco, Shelton, CT (US); Carey M. Tedesco, Shelton, CT (US); Robert C. Tedesco, Trumbull, CT (US); James A. Jorasch, New York, NY (US); Russell P. Sammon, San Francisco, CA (US)

(73) Assignee: HandHold Adaptive, LLC, Shelton, CT (US)

( * ) Notice: Subject to any disclaimer, the term of this patent is extended or adjusted under 35 U.S.C. 154(b) by 478 days.

This patent is subject to a terminal disclaimer.

(21) Appl. No.: 13/657,452

(22) Filed: Oct. 22, 2012

Related U.S. Application Data

(63) Continuation of application No. 12/391,871, filed on Feb. 24, 2009, now Pat. No. 8,296,686.

(60) Provisional application No. 61/195,976, filed on Oct. 14, 2008.

(51) Int. Cl.
*G06F 7/48* (2006.01)
*G06F 3/12* (2006.01)
*G06F 19/00* (2011.01)

(52) U.S. Cl.
CPC .......... *G06F 3/1253* (2013.01); *G06F 19/3481* (2013.01)

(58) Field of Classification Search
CPC .................. G06F 3/1253; G06F 19/3481
See application file for complete search history.

(56) References Cited

U.S. PATENT DOCUMENTS

| | | | |
|---|---|---|---|
| 5,544,649 A | 8/1996 | David et al. | |
| 5,580,254 A | 12/1996 | Ramsey | |
| 5,890,905 A | 4/1999 | Bergman | |
| 6,031,455 A | 2/2000 | Grube et al. | |
| 6,042,383 A | 3/2000 | Herron | |
| 6,056,549 A | 5/2000 | Fletcher | |
| 6,139,494 A | 10/2000 | Cairnes | |
| 6,168,569 B1 | 1/2001 | McEwen et al. | |
| 6,246,992 B1 | 6/2001 | Brown | |
| 6,282,441 B1 | 8/2001 | Raymond et al. | |

(Continued)

OTHER PUBLICATIONS

Non-Final Office Action for U.S. Appl. No. 12/706,020 mailed Oct. 23, 2014, 7 pages.
Non-Final Office Action for U.S. Appl. No. 12/706,020, mailed Jun. 20, 2014, 8 pages.
Attainment Company, "Picture Cue Dictionary," Jun. 16, 2009, 1 page, http://www.synapseadaptive.com/attainment/special/ca/cd.html.

(Continued)

*Primary Examiner* — William Bashore
*Assistant Examiner* — Rayeez Chowdhury
(74) *Attorney, Agent, or Firm* — Withrow & Terranova, PLLC

(57) ABSTRACT

An aid for developmentally disabled individuals takes the form of a mobile terminal having software capable of creating graphical schedules, graphical countdown timers, and graphical choice selections. A caregiver may dynamically program and save schedules which present a graphical sequence of events to the disabled individual to assist the disabled individual in adjusting to the changing events of the day. Likewise, the countdown timer may assist the individual in preparing for an upcoming transition in environment or activity. Still further, the graphical choice selections may help a nonverbal individual express themselves to a caregiver.

17 Claims, 28 Drawing Sheets

(56) References Cited

U.S. PATENT DOCUMENTS

| | | |
|---|---|---|
| 6,314,405 B1 | 11/2001 | Richardson |
| 6,724,298 B2 | 4/2004 | Smith |
| 6,828,989 B2 | 12/2004 | Cortright et al. |
| 7,117,235 B2 | 10/2006 | Cannon et al. |
| 7,217,133 B2 | 5/2007 | Thomas et al. |
| 7,407,484 B2 | 8/2008 | Korman |
| 7,761,322 B2 | 7/2010 | Nakamura et al. |
| 7,836,400 B2 | 11/2010 | May et al. |
| 8,296,686 B1 | 10/2012 | Tedesco et al. |
| 2001/0020904 A1 | 9/2001 | Dayle |
| 2002/0091664 A1 | 7/2002 | Larder et al. |
| 2002/0142271 A1 | 10/2002 | Curtin |
| 2003/0064758 A1 | 4/2003 | Mizuta et al. |
| 2004/0122297 A1 | 6/2004 | Stahmann et al. |
| 2004/0186772 A1 | 9/2004 | Kawatahara |
| 2005/0059034 A1 | 3/2005 | Tyler et al. |
| 2005/0090298 A1 | 4/2005 | Park et al. |
| 2005/0222272 A1 | 10/2005 | Chez |
| 2006/0089545 A1 | 4/2006 | Ratjen et al. |
| 2006/0189278 A1 | 8/2006 | Scott |
| 2007/0117073 A1 | 5/2007 | Walker et al. |
| 2008/0031426 A1 | 2/2008 | Weeks |
| 2008/0038698 A1 | 2/2008 | Meissner et al. |
| 2008/0122796 A1 | 5/2008 | Jobs et al. |
| 2009/0125333 A1 | 5/2009 | Heywood et al. |
| 2009/0131758 A1 | 5/2009 | Heywood et al. |
| 2009/0144089 A1 | 6/2009 | Heywood et al. |
| 2009/0198511 A1 | 8/2009 | Boehlke |
| 2010/0167255 A1 | 7/2010 | Shane et al. |

OTHER PUBLICATIONS

Attainment Company, "Picture Cue Dictionary: Spectronics—Inclusive Learning Technologies," Jun. 16, 2009, 4 pages, http://spectronicsinoz.com/product/21919.

Time Timer, "Tangible time management products," Jun. 16, 2009, 4 pages, http://www.timetimer.com/products.php.

Icon Talk Products, "Schedule Strips," Jun. 16, 2009, 1 page, http://www.icontalk.com/product_cdphp.

Icon Talk Products, "Super Symbols to Go," Jun. 16, 2009, 1 page, http://www.icontalk.com/IT-2.html.

Tangible Time Management, "Time Timer CD," Jun. 16, 2009, 2 pages, http://www.timetimer.com/product_cdphp.

Teaching Tools for Kids With Autism, "Welcome to JoeSchedule's Visual Toolkit," Introduction Video, Jun. 16, 2009, 1 page, http://www.joeschedule.com/js2col_index01.htm.

Abbott, "FDA Approves Abbott's Freestyle Navigator Continuous Glucose Monitoring System," Mar. 13, 2008, 3 pages, www.abbottdiabetescare.com/adc_dotcom/url/content/en_US/10:10/general_content/General_Content_0000163.htm.

Advanced Multimedia Devices, "AMDI—Tech/Touch—New Dynamic AAC Display Specification AMDI Inc," Jun. 6, 2009, 2 pages, http://amdi.net/TTFreedom.html.

Asthmamd, "App Store," 1 page, Accessed Dec. 13, 2011, http://asthmamd.org/3resources/iphone_chart.jpeg.

Autism E-News, "Autism and Assistive Technoology," Apr. 2004, vol. 1 issue 3, 8 pages, http://www.ttac.odu.edu/Enewsarchives/autism/autism_e_april_2004_toc.

Autoworks, "About Autoworks," 2004-2009, 2 pages, http://autoworks.hms.harvard.edu.

Bee Visual, "Choiceworks products," Jun. 16, 2009, 2 pages, http://www.beevisual.com/choiceworks.html.

Behaviortracker, "Behavior Tracker Pro Receives Coverage on NBC," Jan. 29, 2010, 3 pages, www.behaviortrackerpro.com.

Breen, "The iphone Pocket Guide," Sep. 29, 2007, Peachpit Press, pp. 194.

Ddtrac, "Ddtrac Data Collection and Progress Monitoring Software," 2007-2010, 1 page, www.developingmindssoftware.com/product.

Do2Learn, "Educational Resources for Special Needs," Jun. 16, 2009, 2 pages, http://www.do2learn.com/games/dragndrop/timesequence/index.htm.

Dynavox & Mayer-Johnson, "M3-Feateures," Jun. 16, 2009, 2 pages, http://www.dynavoxtech.com/products/m3/features.aspx.

Dynavox & Mayer-Johnson, Products—Education Software, "Boardmaker Plus!," 2 pages, http://dynavoxtech.com/products/education/bm-plus.aspx.

Final Office Action mailed Jan. 19, 2012, for U.S. Appl. No. 12/551,186, 39 pages.

Harvard, "The Wall Lab," Accessed Dec. 13, 2011, 2 pages, http://wall.hms.harvards.edu/research.

Kim, S. et al., "Digital Picture Scheduler: An Everyday Activity Sharing Tool for Parents of Children with Autism," School of Interactive Computing, GVU Center, Georgia Institute of Technology, 1 page.

Mobile Thinking, "Introducint mTrial," 2008, 1 page, www.mobilethinking.com/dtm.

Nature, "Personal Technology: Phoning in Data," Apr. 22, 2009, 2 pages, www.nature.com/news/2009/090419/full/458959a.html.

Overboard—Communication Overboard, Designed by Gus communication Devices, Inc., Jun. 16, 2009, 4 pages, http://www.gusinc.com/Overboard/index.html.

Patients Like Me, "Patients Helping Patients Live Better Every Day," Accessed Dec. 13, 2011, 1 page, www.patientslikeme.com.

Picture Planner, "Icon-based personal planning," 1 page, http://erinstitute1001.qwestoffice.net/picture_planner/detail.html, Jun. 16, 2009.

Qcharm, Portable & Visual Cuing System, 1 page, http://www.qcharm.com/index.html, Jun. 16, 2009.

Schwartz, I et al., "Including Children with Autism in Inclusive Preschools: Strategies that Work," 11 pages, http://www.newhorizens.org/speneeds/inclusion/information/schwartz2.htm, Jun. 6, 2009.

Silver Lining Multimedia, "Picture This . . . Series," 3 pages, http://www.silverliningmm.com/ptframe.html, Jun. 18, 2009.

sourceforge.net: Community Discussion Forums, "Picture Schedule Program (5 posts)," 3 pages, http://sourceforge.net/community/forum/topic.php?id=2214&page, Jun. 16, 2009.

Symtrend, "Electronic Diaries and graphic tools for health care and special education," Accessed Dec. 13, 2011, 1 page, https://www.symtrend.com/tw/public/.

TC 50, "Sekai Camera for Social Tagging on the iPhone," 2 pages, http://www.techerunch.com/2008/09/09tc50-sekai-camera-for-social-tagging-on-the-iphone . . . .

Techcrunch, "AsthmaMD helps asthma sufferers, gathers aggregate research data," Jan. 10, 2010, 3 pageshttp://techcrunch.com/2010/01/10/asthmamd-helps-asthma-suffers-gathers-aggregate-research-data.

Technology Review, "Cell phones that listen and learn," Jun. 22, 2009, 3 pages, www.technologyreview.com/communications/22907.

Quinnipiac University, "Pearson's r Correlation," Feb. 12, 2001, 1 page, http://web.archive.org/web/20010212103243/http://faculty.quinnipiac.edu/libarts/polsci/Statistics.html.

Online Statistics, "Values of the Pearson Correlation," Jul. 20, 2006, 3 pages, http://web.archive.org/web/20060720192353/http://onlinestatbook.com/chapter4/person.html.

Non-Final Rejection mailed Mar. 29, 2012, for U.S. Appl. No. 12/706,020, 22 pages.

Final Office Action for U.S. Appl. No. 12/706,020 mailed Nov. 14, 2012, 29 pages.

Non-final Office Action mailed Oct. 7, 2011 for U.S. Appl. No. 12/551,186, 14 pages.

Non-final Office Action mailed Aug. 25, 2011 for U.S. Appl. No. 12/551,186, 7 pages.

Non-final Office Action mailed Apr. 14, 2011 for U.S. Appl. No. 12/391,871, 24 pages.

Final Office Action mailed Oct. 18, 2011 for U.S. Appl. No. 12/391,871, 35 pages.

Final Office Action for U.S. Appl. No. 12/706,020, mailed Mar. 26, 2015, 10 pages.

| IMAGE NAME 352 | CATEGORY 354 | USED IN SCHEDULE 356 | USED IN COUNTDOWN 358 | USED IN CHOICE 360 |
|---|---|---|---|---|
| DOG.jpg | ACTIVITIES; PETS | AFTER SCHOOL | --- | --- |
| TOOTHBRUSH.jpg | MEAL TIME; SELF CARE | SUPPER | BEDTIME | --- |
| HAPPY.jpg | EMOTIONS | --- | --- | GRUMPY FACE |
| ○○○ | ○○○ | ○○○ | ○○○ | ○○○ |
| UMBRELLA.jpg | DAYS & WEATHER | --- | --- | --- |

PORTABLE PROMPTING AID FOR THE DEVELOPMENTALLY DISABLED

PRIORITY APPLICATIONS

The present application is a continuation of U.S. patent application Ser. No. 12/391,871 filed on Feb. 24, 2009 entitled "PORTABLE PROMPTING AID FOR THE DEVELOPMENTALLY DISABLED", now U.S. Pat. No. 8,296,686, which is hereby incorporated by reference in its entirety.

The parent application claims priority to U.S. Provisional Patent Application Ser. No. 61/195,976, filed 14 Oct. 2008, which is also hereby incorporated by reference in its entirety.

FIELD OF THE INVENTION

The present disclosure is directed to providing devices, systems and methods for providing a sensory aid for the developmentally disabled.

BACKGROUND

With a growing population, the number of developmentally disabled children grows. Additionally, the rates at which children have been diagnosed as developmentally disabled, and particularly diagnosed with autism, have steadily increased. While there is a continuum of disabilities that fall under the general heading of developmentally disabled, many individuals that are developmentally disabled experience difficulty in developing normal speech and language abilities and may also suffer from sensory processing dysfunction (SPD). SPD encompasses those situations where a person has one or more senses that are hyposensitive or hypersensitive.

These dysfunctions and their manifestations make it difficult for such individuals to adapt to dynamic settings and in particular they may have difficulty transitioning between activities. This difficulty is compounded by the aforementioned language barriers that may exist.

Conventional approaches have not been able to provide a convenient tool that allows caregivers to communicate effectively with such individuals and prepare such individuals for known upcoming changes, especially in contexts such as ordinary life in the community, which is markedly more dynamic and rich with sensory stimuli as compared to relatively sterile and controlled therapeutic settings.

BRIEF DESCRIPTION OF THE DRAWINGS

FIG. 26 illustrates a first exemplary database suitable for use with the present disclosure.

DETAILED DESCRIPTION

A mobile terminal with a display screen may be used with the software described herein to allow caregivers to create a schedule using appropriate graphical elements, which may be presented to the disabled individual so that the disabled individual may be graphically prepared for upcoming transitions or changes. Likewise, the caregiver may program graphical timers for use with the disabled individual so that the disabled individual has a graphical indication of an amount of time remaining until a change in activity is to occur. Such timers may be incorporated into the schedule so that as a transition nears, a timer may be displayed to the disabled individual. Still further the caregiver may program the mobile terminal to display two graphical elements for display to the disabled individual from which the disabled individual may select a choice. During creation of these graphical tools, the caregiver may be given the opportunity to select the images by selecting images from predefined categories of thematically-linked images. The image grouping may facilitate dynamic creation of the graphical tools and/or allow the disabled individual to participate in the creation of the graphical tools.

Still other graphical prompts may be programmed by the caregiver to facilitate graphical interaction rather than oral interaction with the disabled individual. Likewise, new graphical elements may be captured by a camera either internal to the mobile terminal or external to the mobile terminal and uploaded to the mobile terminal. Likewise, video, audio or other elements (e.g., vibration output) may be incorporated into the schedule, timers, or choices so as to facilitate communication with the disabled individual.

The use of a mobile terminal provides a highly portable, stylish, and malleable tool through which caregivers may adjust to the dynamic surroundings of the disabled individual and provide customized graphical elements to assist in communicating with the disabled individual.

Figure 1:
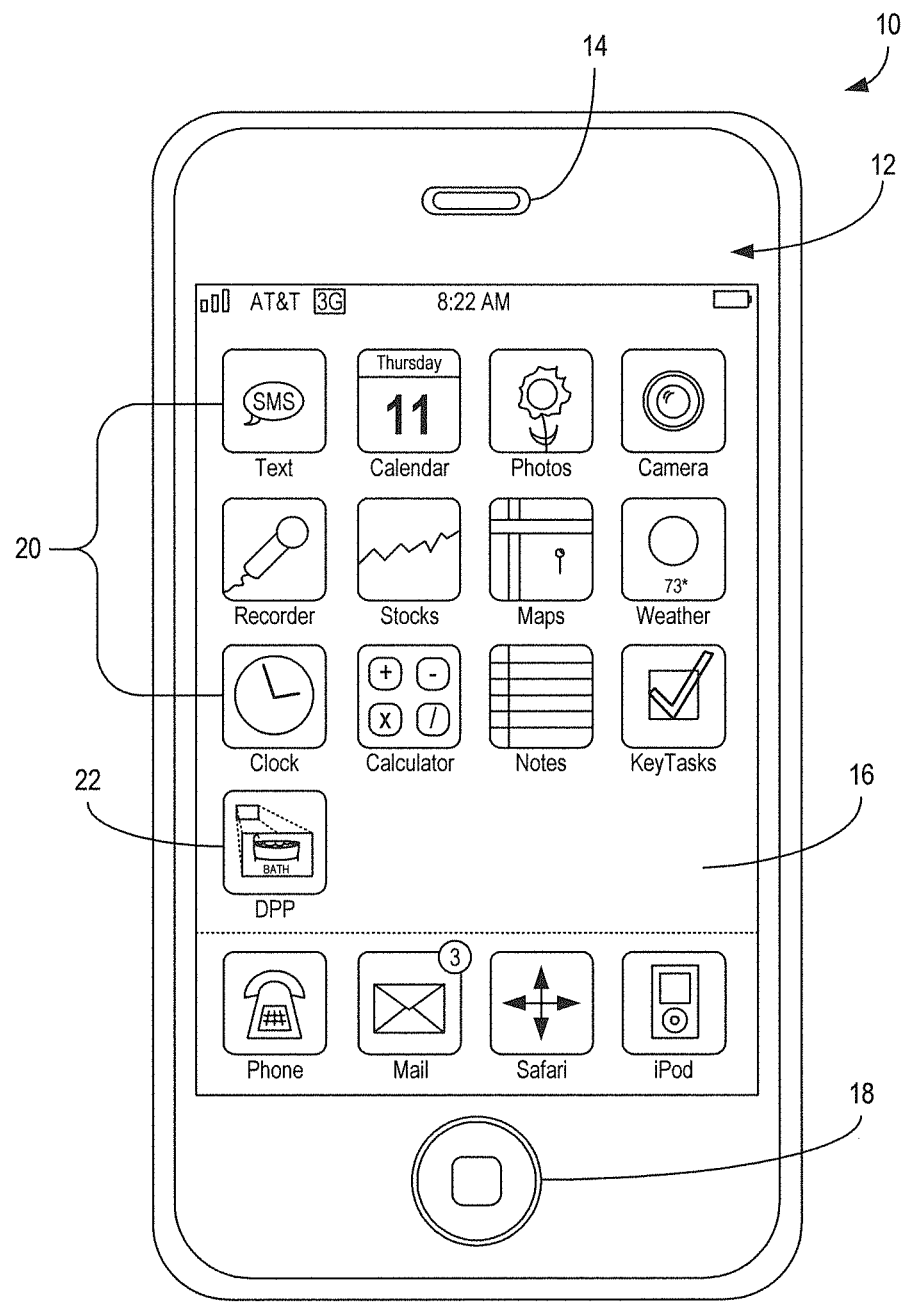
FIG. 1 illustrates a front elevational view of a mobile terminal.

An overview of some of the hardware elements is provided before addressing some of the methods and potential screen configurations associated with embodiments of the present disclosure. A mobile terminal 10 is illustrated in FIG. 1. An exemplary suitable mobile terminal 10 may be the APPLE® IPHONE™ (or IPOD™) and may include a user interface 12 that includes a speaker 14, a microphone 26 (FIG. 2), a touch screen display 16, and a command entry button 18. One or more icons 20 may be displayed on the touch screen display 16. The user may enter commands by touching an icon on the touch screen display 16 or by using the command entry button 18 as is well understood. One such icon 22 may launch software that effectuates embodiments of the present disclosure. In one embodiment, the software is developed by a third party. The practice of third-party software development on the IPHONE™ platform is commonplace today, with tens of thousands of applications available for sale through the APPLE® APP STORE, and other mobile terminal manufacturers are embracing such third-party development of mobile software applications. Thus, while the IPHONE™ is particularly contemplated, the disclosure is not so limited, and any readily portable handheld computing device may be appropriate including personal digital assistants, cellular telephones, WINDOWS MOBILE™ enabled devices (e.g., the HTC TOUCH DIAMOND™), or the like. Further specific examples of such mobile terminals include the BLACKBERRY™ line of wireless devices manufactured by Research in Motion of Waterloo, Ontario, Calif.; the T-MOBILE G1 or other mobile terminals operating on the ANDROID platform developed by Google, Inc. of Mountain View, Calif.; the PRADA™ or other mobile terminals manufactured by LG ELECTRONICS MOBILECOMM U.S.A., INC. of San Diego, Calif.; the INSTINCT™ or other mobile terminals manufactured by SAMSUNG TELECOMMUNICATIONS AMERICA, LLC; the XPERIA™ X1 or other mobile terminals manufactured by SONY ERICSSON MOBILE COMMUNICATIONS AB of Sweden; the N96 or other mobile terminals manufactured by NOKIA GROUP of Finland; the PRE™ or other mobile terminals manufactured by PALM, INC. of Sunnyvale, Calif., or the like. Software of the present disclosure may operate in conjunction with any of these hardware platforms, or in conjunction with any platforms similar to these.

Figure 2:
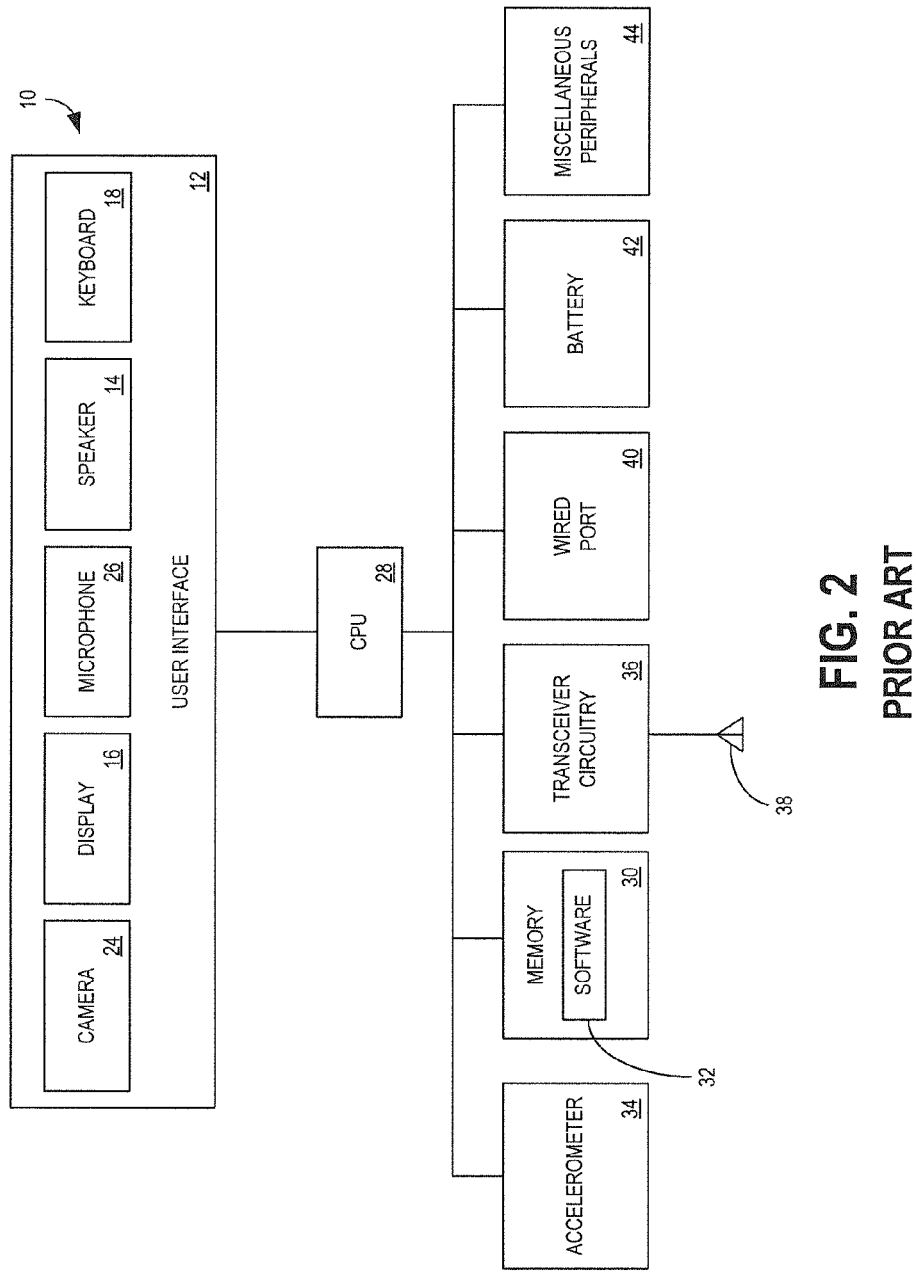
FIG. 2 illustrates a block diagram of the components of a conventional mobile terminal.

A block diagram of the mobile terminal 10 is illustrated in FIG. 2. The mobile terminal 10 includes the elements already illustrated and further includes, within the user interface 12, a camera 24 and the aforementioned microphone 26. The user interface 12 is operatively coupled to a central processor (CPU) 28. The CPU 28 is also operatively coupled to memory 30 with software 32 stored therein, an accelerometer 34, transceiver circuitry 36, which in turn is coupled to an antenna 38, one or more wired ports 40, a battery 42, and any other miscellaneous peripherals 44 as is common in the mobile terminal industry (e.g., an internal clock, a vibration unit, a GPS receiver, a thermometer, pressure sensor, a light sensor, an infrared sensor, a temperature sensor, a motion detector, an altimeter, a radio frequency identification (RFID) transponder or receiver, or the like).

Figure 3:
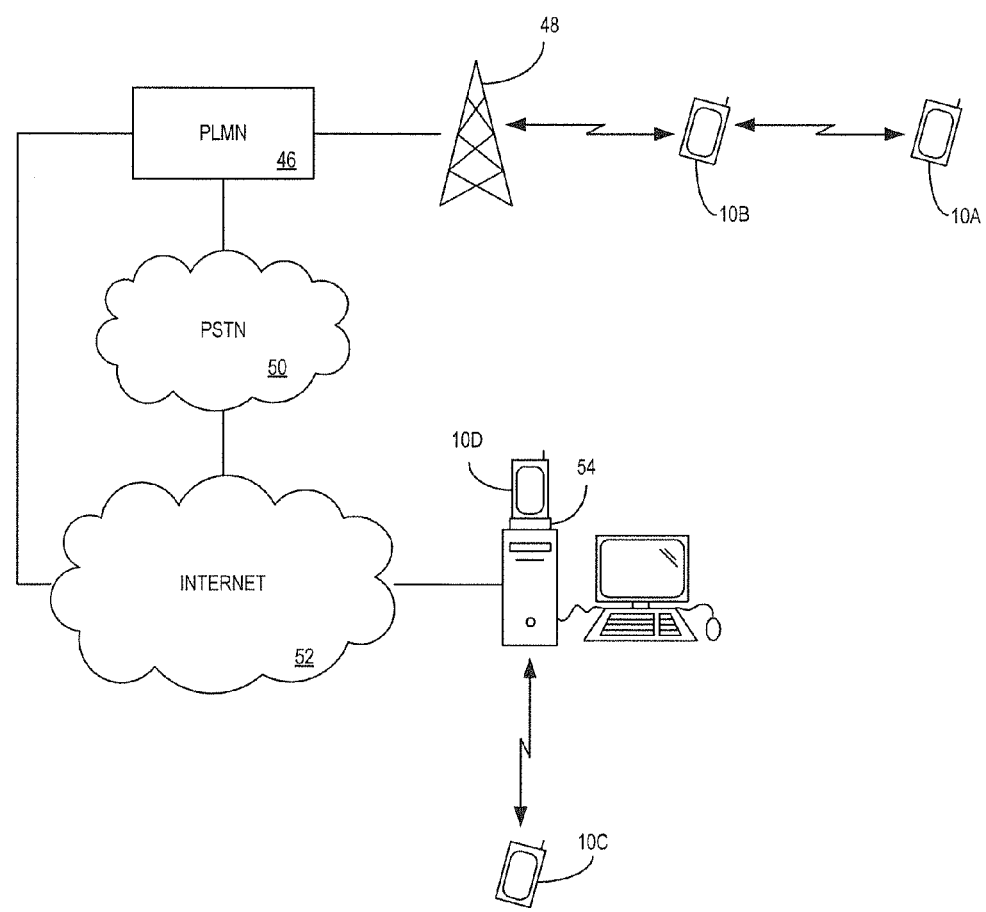
FIG. 3 illustrates a variety of networks in which a mobile terminal may operate.

FIG. 3 illustrates a variety of networks through which mobile terminals 10 may communicate. For example, a first mobile terminal 10A may communicate with a second mobile terminal 10B through a local wireless network such as a BLUETOOTH™, infrared, or other short range communication protocol. Additionally, or alternatively, the second mobile terminal 10B may communicate with a cellular network such as the Public Land Mobile Network (PLMN) 46 through a cellular base station 48. The PLMN 46 may communicate with the Public Switched Telephone Network (PSTN) 50 and/or the Internet 52. One or more computers 54 may be communicatively coupled to the Internet 52 and may include a wireless transceiver to communicate wirelessly with a third mobile terminal 10C or a docking station 56 to communicate via a wired line with a fourth mobile terminal 10D. More information on networks and communication protocols can be found in the Rules of Interpretation and General Definitions set forth below. Suffice to say that the particular network or communication protocol is not central to embodiments of the present disclosure.

Figure 4:
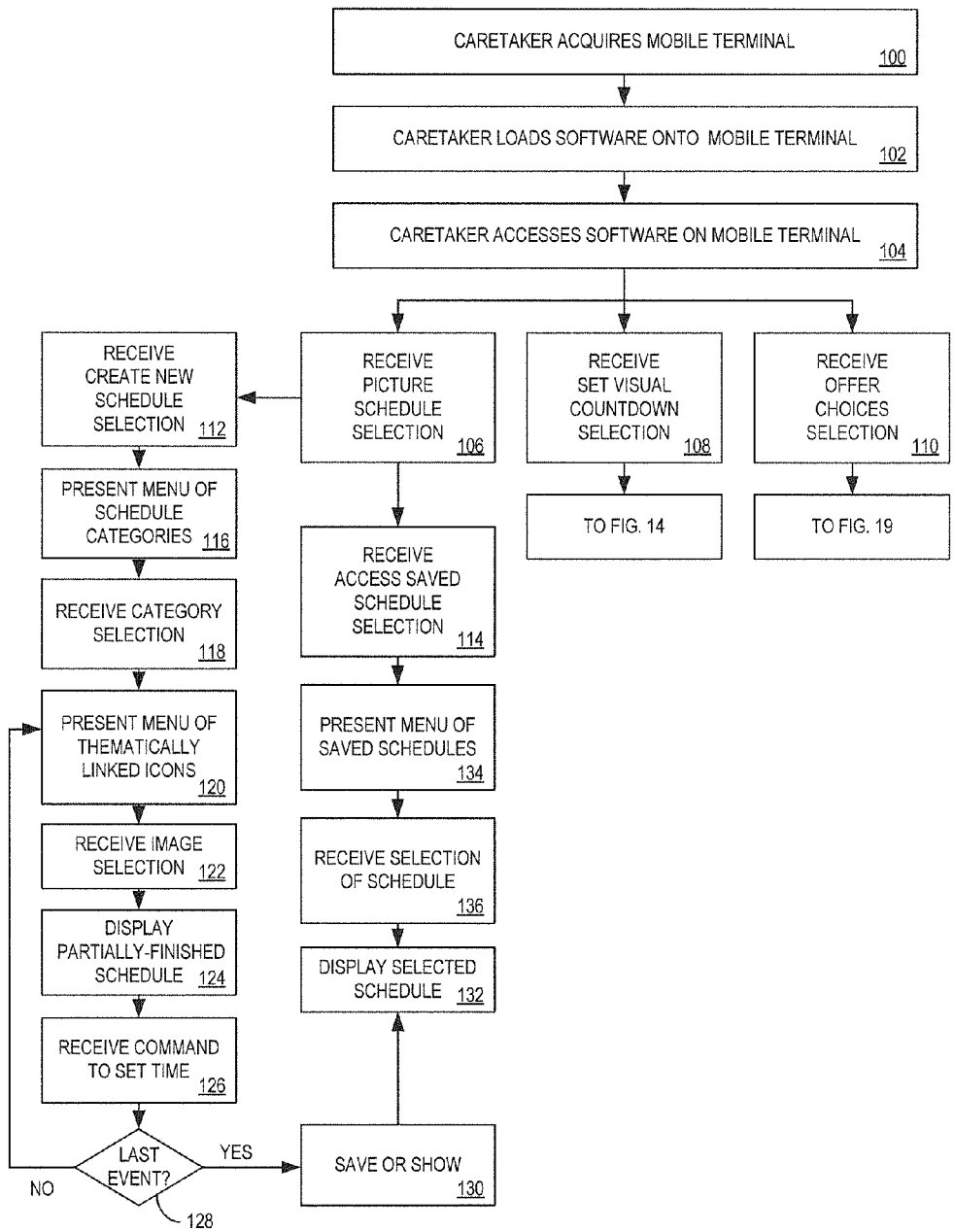
FIG. 4 illustrates a first flow chart showing a portion of an exemplary embodiment of the present disclosure.

Against this backdrop of hardware, an overview of an exemplary method is presented starting with reference to FIG. 4 as a flow diagram interspersed with additional Figures for supporting explanatory and exemplary screen shots. Initially, the caregiver acquires a mobile terminal 10 (block 100). This acquisition may be a gift, a purchase, a lease, borrowing, or otherwise. For example, the disabled individual may purchase the mobile terminal 10 and loan it to the caregiver for the purposes of carrying out embodiments of the present disclosure. Alternatively, the caregiver may purchase the mobile terminal 10 for use by and/or with the disabled individual. The caregiver may load the software embodying the present disclosure onto the mobile terminal 10 (block 102). If the mobile terminal 10 has a disk drive or other data storage device or functionality (e.g. flash memory), the software may be loaded from a disk or other source. Otherwise, the software may be loaded onto a computer 54 (e.g., via disk transfer or download) and transferred to the mobile terminal 10 through the docking station 56 or wirelessly. As still another alternative, the mobile terminal 10 may download the software through the PLMN 46 or other technique as desired. The software could be preloaded on the mobile terminal 10 such that when the lease or purchase is made, the software is immediately accessible. The software itself may be free, paid or subsidized in whole or part by a third party (such as a school district or other governmental agency or private foundation). Note that while it is contemplated that the caregiver performs these and other steps, it is also possible that the disabled individual performs these and the other steps.

Figure 5:
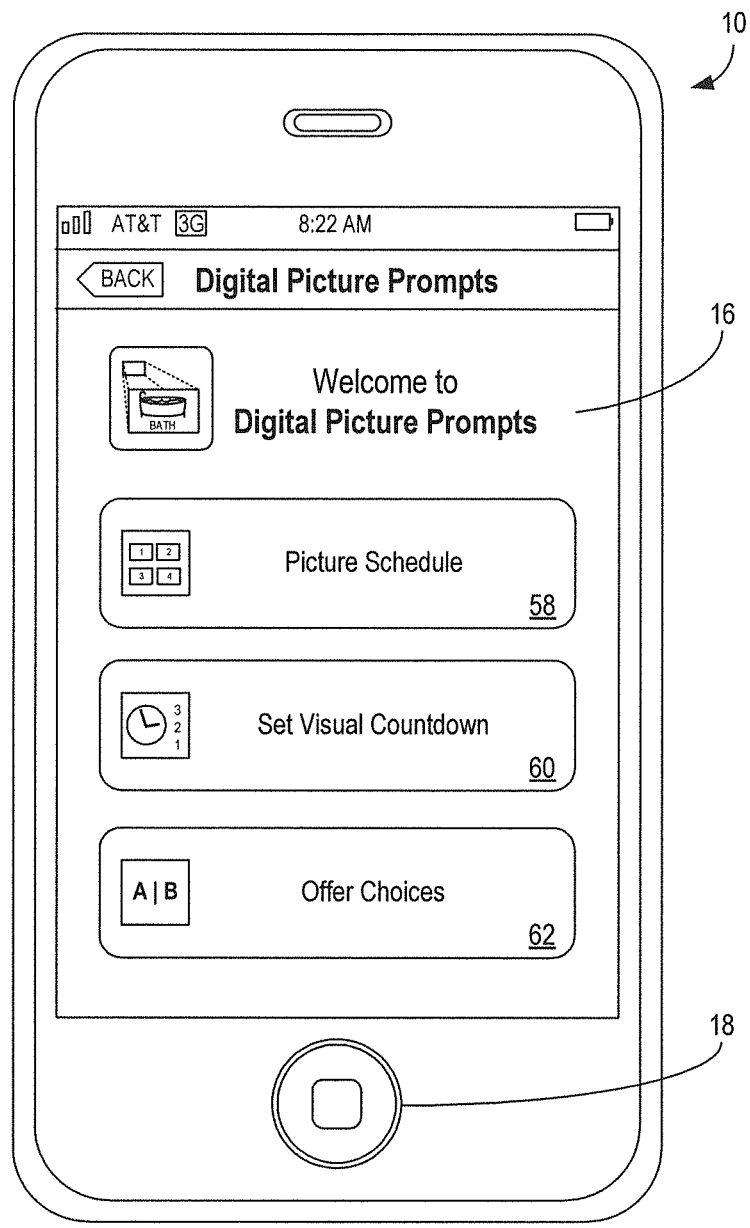
FIG. 5 illustrates a first screen shot showing a screen shot associated with the flow chart of FIG. 4.
Figure 6:
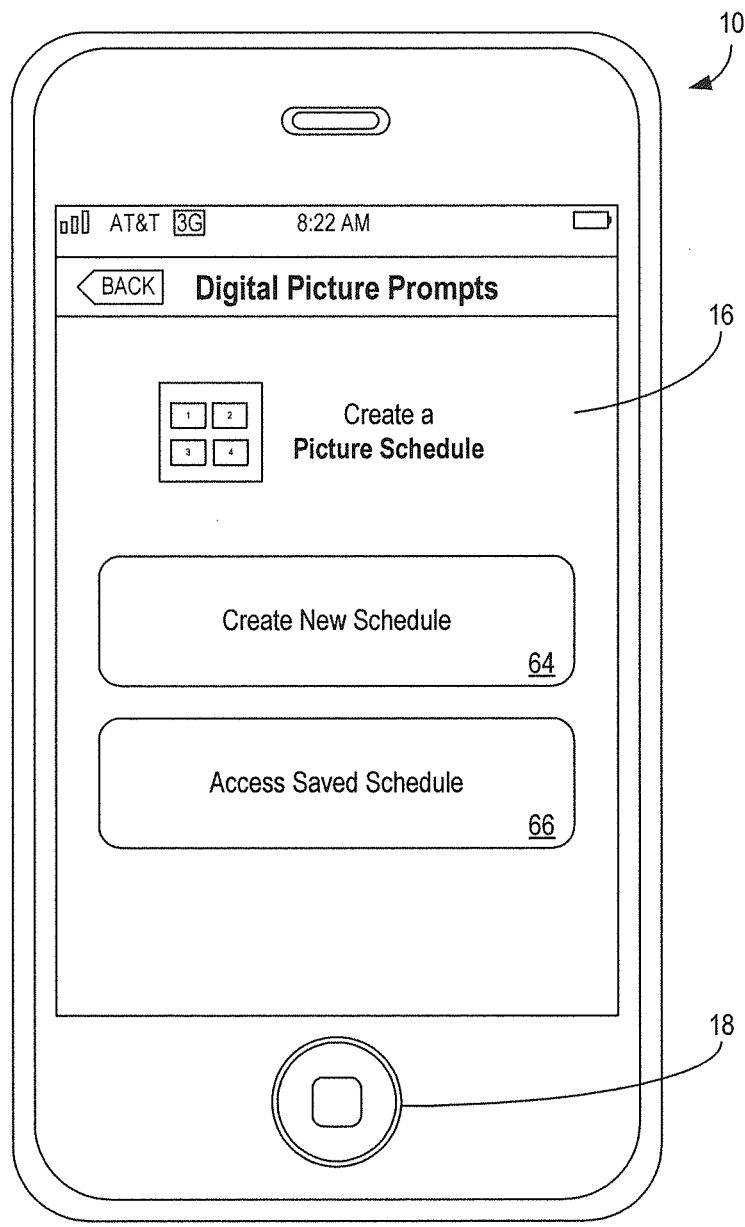
FIG. 6 illustrates a second screen shot associated with the flow chart of FIG. 4.

The caregiver accesses the software through the user interface 12 of the mobile terminal 10 (block 104), such as by tapping the appropriate icon 22 on the display 16. Activating the software may call up a screen such as that illustrated in FIG. 5, where the software causes a number of choices to be displayed to the user. The choices, in this exemplary embodiment, comprise picture schedule (block 106, FIG. 4; icon 58 FIG. 5); set a visual countdown (block 108, FIG. 4; icon 60 FIG. 5); and offer choices (block 110, FIG. 4; icon 62, FIG. 6). The user may select an appropriate icon by touching the display 16 at an appropriate location, scrolling through the prompts with the command button 18, or other technique as desired.

Figure 7:
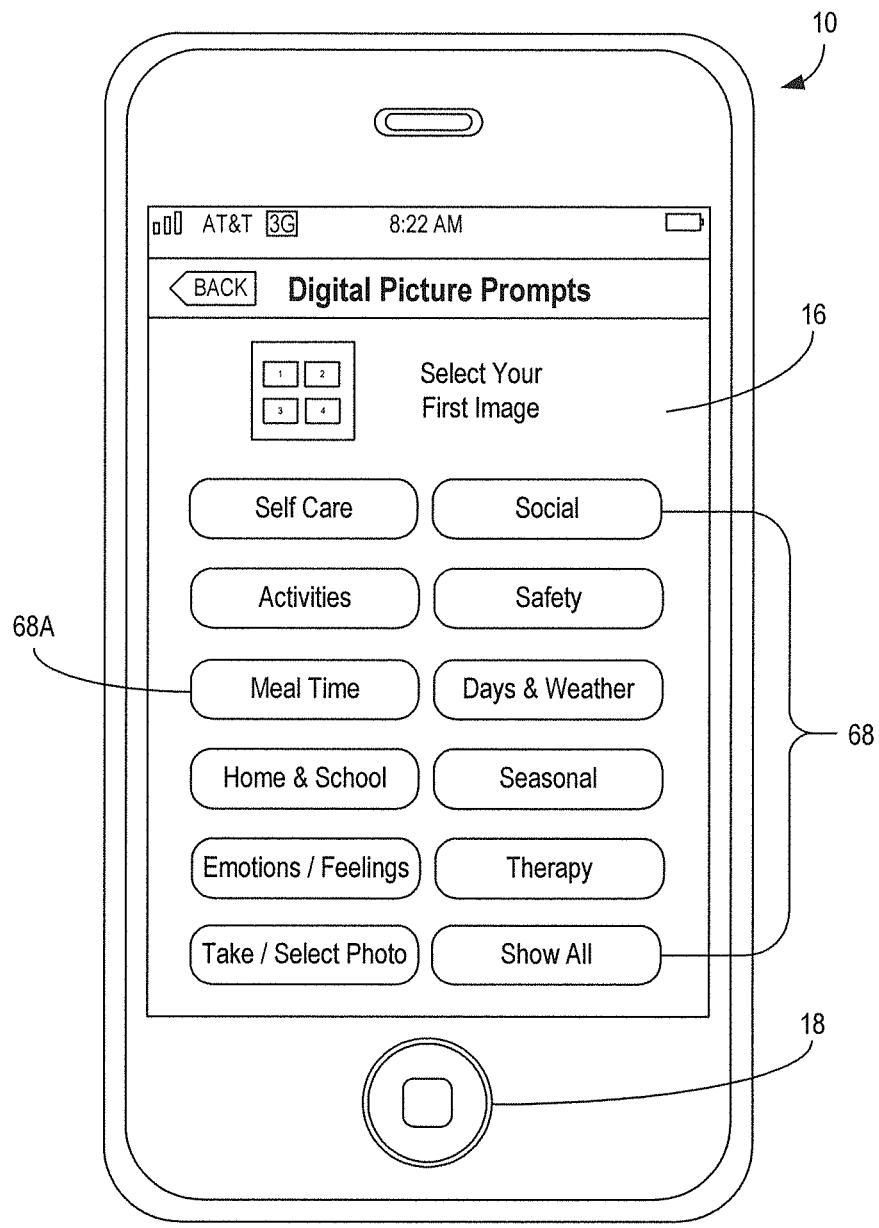
FIG. 7 illustrates a third screen shot associated with the flow chart of FIG. 4.

To continue the example, assume the user selects picture schedule at block 106. A screen shot, such as that illustrated in FIG. 6 may appear. The user may be offered the choices of creating a new schedule (block 112, FIG. 4, icon 64, FIG. 6) or accessing a saved schedule (block 114, FIG. 4, icon 66, FIG. 6). If the user selects create a new schedule, the mobile terminal 10 may display a screen shot such as that illustrated in FIG. 7, wherein icons 68 for various schedule categories are presented (block 116, FIG. 4). The user may select an appropriate icon 68, (causing the control system to receive the selection (block 118)) such as icon 68 for meal time to start creating a schedule that is thematically linked to the category of a meal time or at a minimum view images that are thematically linked to the category for inclusion in a schedule. An alternate approach, wherein the first user indicates a time and subsequently selects an associated icon (perhaps from a category of icons) is also contemplated. Additionally, rather than select a stored image, the user may elect a "take photo now" (or similarly labeled) option (not shown), take a picture of a proximate element, and utilize this digital snapshot in the creation of a schedule.

Figure 8:
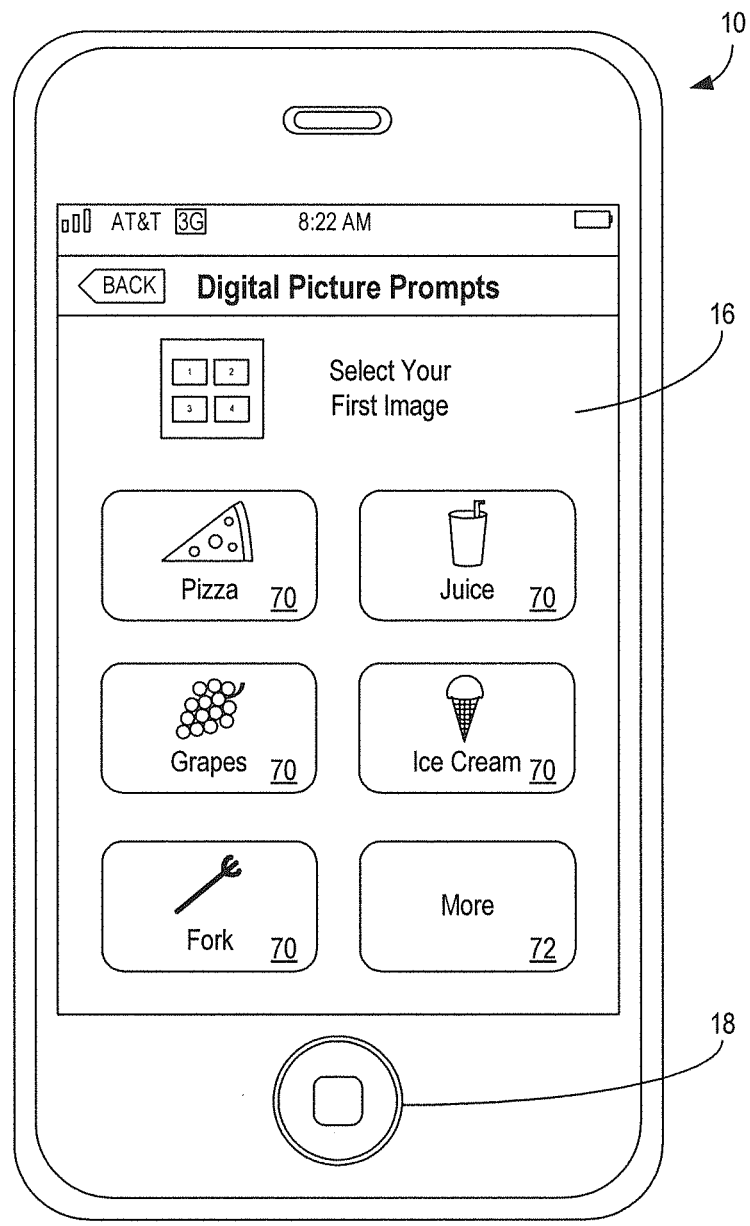
FIG. 8 illustrates a fourth screen shot associated with the flow chart of FIG. 4.

Once the category has been selected, the control system may display a screen shot such as that illustrated in FIG. 8, with icons 70 comprising images that are thematically-linked to the category and represent various events or elements that might be part of the schedule being created (block 120). In the example, the user has selected a meal time icon 68A, so the icons 70 are images of food items or eating utensils. Additionally, a "more" icon 72 may be presented so that the user may select different icons. Alternatively, the command button 18 or touch screen function within the display 16 may allow the user to scroll through a menu of icons that exceeds a single screen (e.g., the IPHONE™ allows a touch-based scroll command to accommodate such actions).

When the user sees the image corresponding to an event within the schedule under creation, the user may select that image (block 122). Receiving the selection may cause the control system to display a screen shot with the partially assembled schedule (block 124) such as that illustrated in FIG. 9. As illustrated, the selected image populates into a first slot 74 within the schedule being created. The schedule being created prompts the user to enter a time with a time prompt icon 76. The schedule being created has further slots 78 for additional events or elements within the schedule. The further slots 78 may be filled by using a command such as "add another image" command 80. Additionally, if the user is done creating the schedule, a command such as "finish and show schedule" icon 82 may be used. While it is contemplated that images are added to the bottom of the schedule, a user preference may allow them to be added to the top of the schedule, or between already existing images within the schedule. Note further that a user may select a plurality of images from a menu and add all of them substantially at the same time. Likewise, a user may shift between categories of images during schedule creation such that, for example, a first image is selected from a meal time category and a second image is selected from a clothing category. Appropriate navigation command buttons may allow the user to go back and forth between categories, images, and the like.

Figure 10:
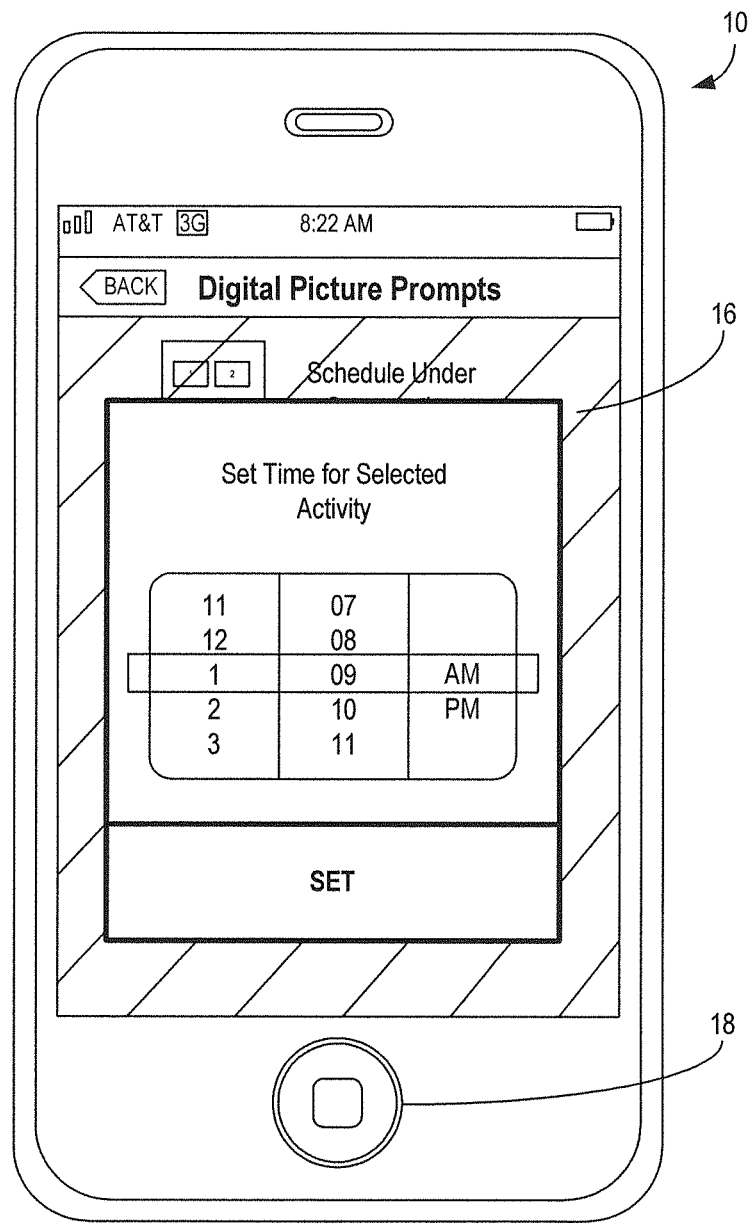
FIG. 10 illustrates a sixth screen shot associated with the flow chart of FIG. 4.

For the sake of the continued example, the user optionally selects the time prompt icon 76 (block 126), which in turn may launch a time entry screen such as illustrated in FIG. 10. The user selects a time for the event in the schedule such as by tapping an hour, and then a minute, and then indicating AM or PM. FIG. 10 illustrates a time entry screen such as used in the IPHONE™ environment, but it should be appreciated that a more traditional time entry may be typed in, incremented/decremented, or the like, (e.g., such as is common in a WINDOWS® operating environment). In some embodiments, the step of entering a time in association with an image may be omitted. For example, caregivers may create graphical schedules simply to present a series of activities irrespective of the exact time of day they are to be performed (e.g., "social stories" demonstrating to disabled persons appropriate steps of interpersonal exchange).

Figure 9:
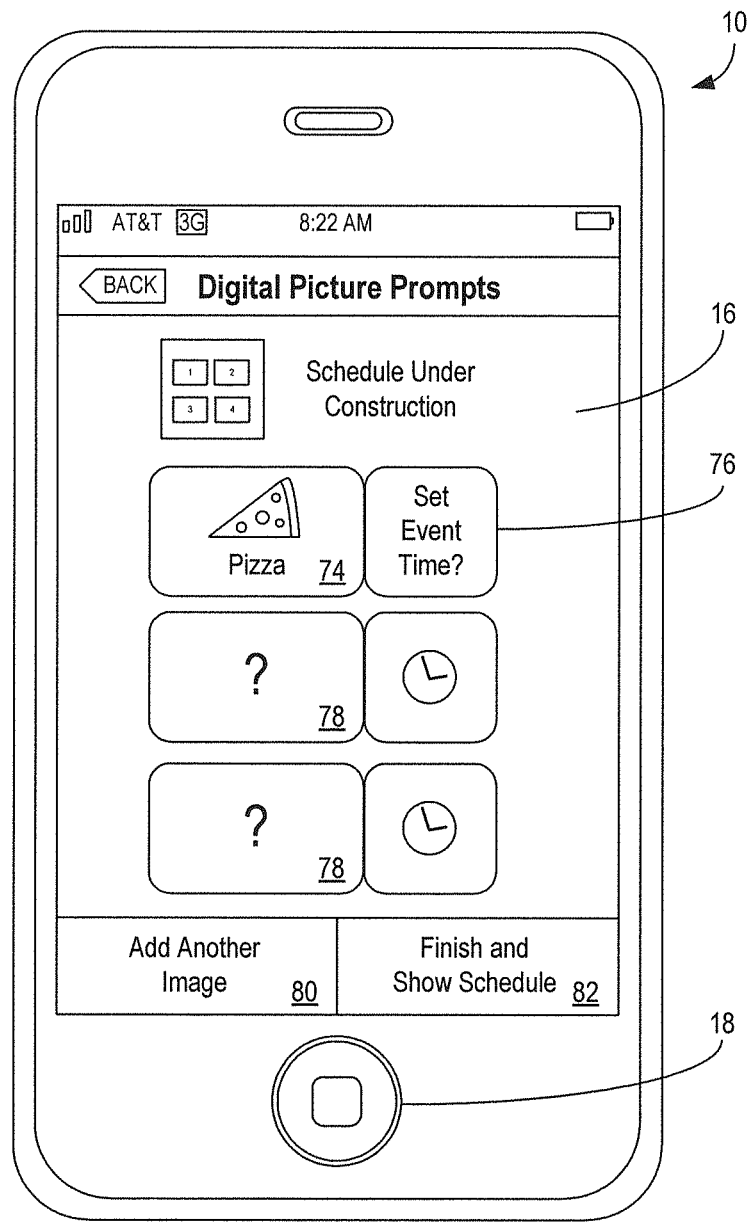
FIG. 9 illustrates a fifth screen shot associated with the flow chart of FIG. 4.
Figure 11:
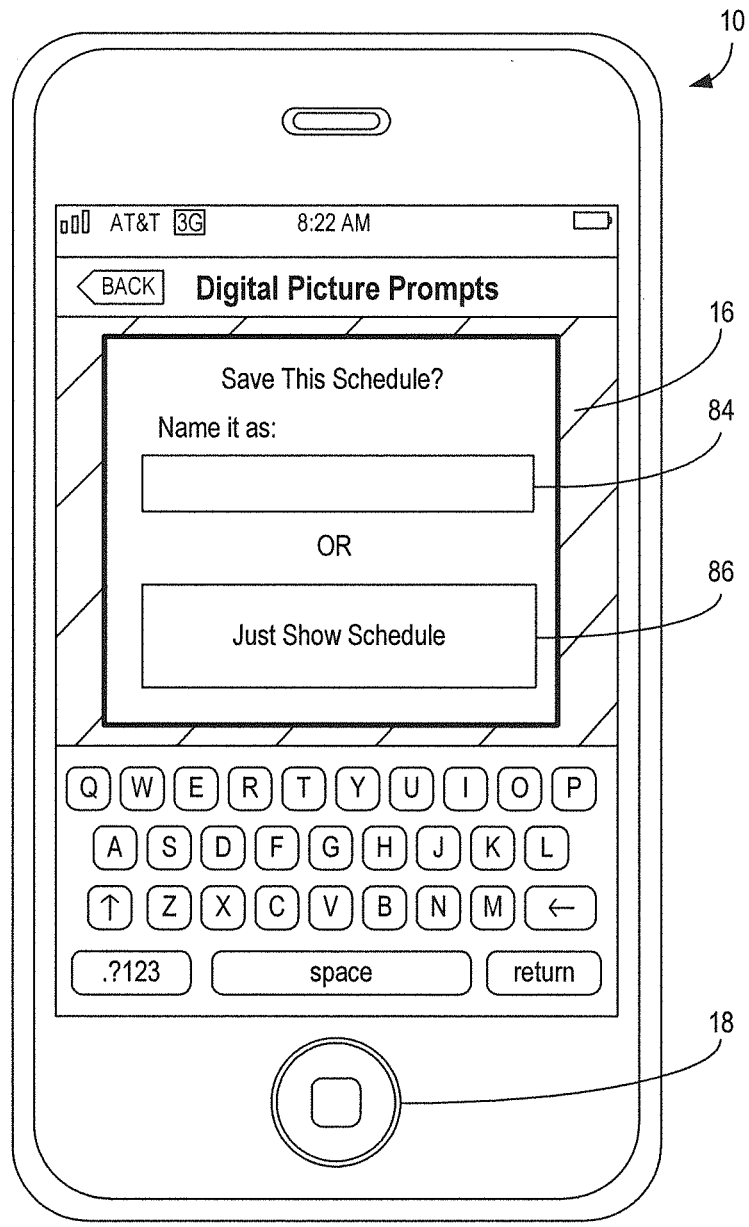
FIG. 11 illustrates a seventh screen shot associated with the flow chart of FIG. 4.

Once the time is entered, the system returns to the screen of FIG. 9 so that the user may indicate whether there are additional events for the schedule (block 128). If the user indicates that another event is to be added, the process repeats as noted. If, however, the user indicates that the schedule is complete, the user may use the "finish and show schedule" icon 82 to proceed to the screen shot of FIG. 11. If the user is finished, then the control system may prompt the user to give the schedule a name under which to save the schedule (icon 84) or to just show the schedule (icon 86) (block 130). A keyboard (whether physical or virtual, such as a touch-screen keyboard) may be provided to enter a name as is well understood. If the user selects show schedule icon 86, then the selected schedule may be displayed (block 132) as illustrated in the screen shot of FIG. 12. Specifically, a graphical schedule 88 may be presented. As is known on the IPHONE™, the orientation of the schedule 88 may rotate according to the orientation in which a person is holding the mobile terminal 10 (note that the other functions described herein may also rotate as the mobile terminal 10 rotates). The selected images 90A-90D provide a graphical schedule for a disabled user to ascertain readily the order in which events are to take place. In the exemplary embodiment, the second user is allowed to have pizza, then a dessert (ice cream), followed by tooth brushing and then bed time. By presenting images of events and a sequence of events, the disabled user may be better prepared to deal with the transition between these activities, which may prevent tantrums or other resistive behavior.

It should be noted that in one or more embodiments, the selected schedule may be suitable for display and presentable graphically to a disabled person at any point once a caregiver has selected at least one image.

Additional command buttons may be enabled, such as a more command 92A, a fewer command 92B, an edit current schedule command 94, or scroll bars 96. More command 92A and fewer command 92B allow the number of images to be controlled so that each image is displayed at a size that is suitable for discernment. The edit current schedule command 94 may take the user back to block 120 so that the user may edit the schedule. Alternately, selection of the edit schedule command 94 may allow for streamlined editing directly through schedule 88; for example, the user may change the order of events within the schedule by "dragging and dropping" them, may delete items from the schedule, or the like, without the need to access a separate menu screen. While FIG. 12 discloses a few particularly contemplated on-screen icons to allow for navigation, other means for navigation may be provided (e.g., an IPHONE™ user utilizes a known "pinch" command on the device's surface to "zoom out" and show more icons than are currently displayed).

When the schedule is actually used, the times that the caregiver has input may be used in conjunction with the internal clock to drive the schedule. For example, if the schedule says that at 7:00, activity X is to occur and at 7:15, activity Y is to occur, then when the internal clock reaches 7:00, the image associated with activity X is display prominently (e.g., alone, larger than the other images, shown under an arrow, flashing, or otherwise highlighted). Then when the clock says it is 7:15, the image of activity X is deemphasized, and the image associated with activity Y is emphasized. If the images are arranged in a scrolling manner, the active image is scrolled to the center location to further emphasize that the event associated with that particular image is occurring. The scrolling images also have the benefit in that the disabled individual may see the smaller, de-emphasized image for the upcoming activity. This visibility may help to warn the disabled individual of an upcoming change and help ease the transition between events. The use of the system clock in this manner helps the schedule advance automatically, so that the disabled individual does not have to check off or otherwise manually advance the schedule throughout the progression of time. In effect, the right images are displayed at the right time for the disabled individual.

Figure 13:
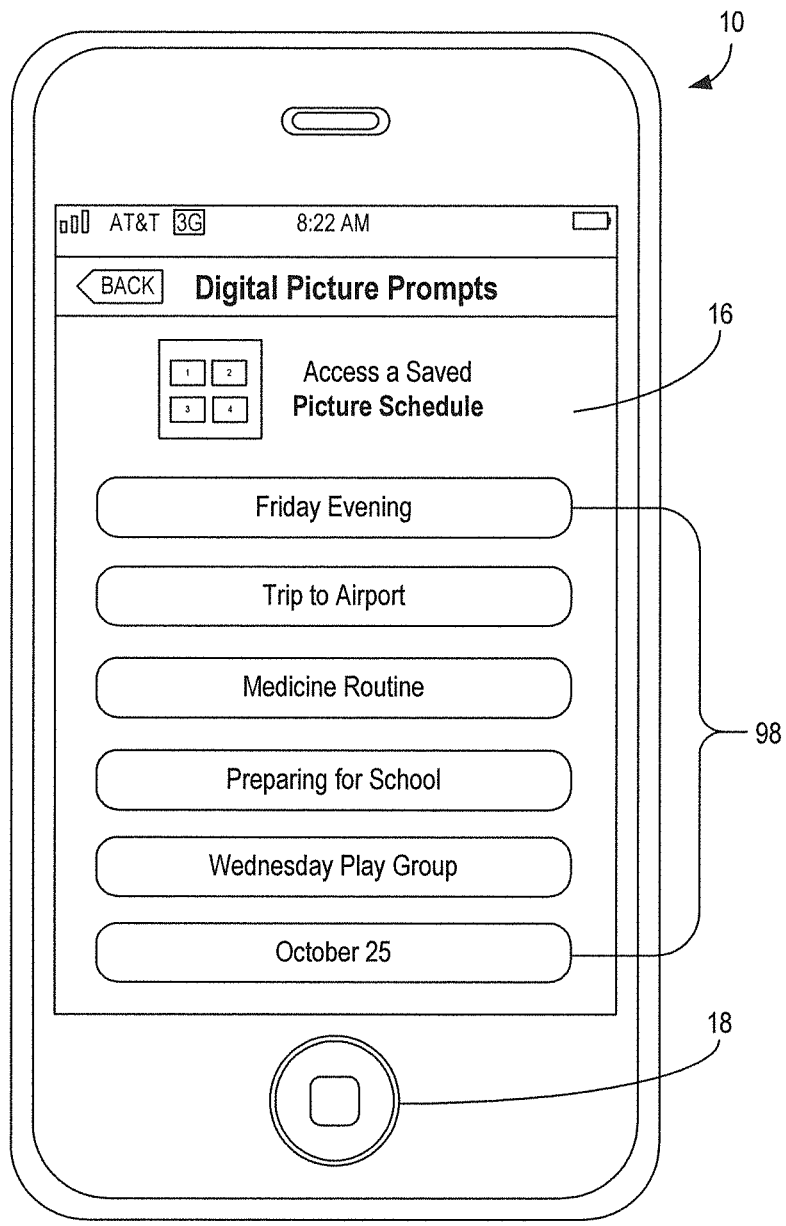
FIG. 13 illustrates a ninth screen shot associated with the flow chart of FIG. 4.

Returning to block 114 of FIG. 4, if the control system receives an access saved schedule selection, the control system may display a list of saved schedule icons 98 (block 134) such as that illustrated in FIG. 13. The user touches or otherwise actuates an icon 98 thereby providing the control system with a selection of a desired schedule (block 136), which in turn causes the selected schedule to be displayed (block 132).

Use of the graphical schedule allows a caregiver to provide nonverbal or otherwise disabled individuals a visual means for understanding what is about to happen to or what is expected of the disabled individual. Such forewarning eases transitions between activities, events, or environments. Likewise, the portable nature of the mobile terminal 10 allows the disabled individual to take the mobile terminal 10 with him throughout the day and refer to the schedule as needed. Furthermore, the portable nature of the mobile terminal 10 means that the caregiver can create schedules dynamically using just the mobile terminal 10. For individuals with slight disabilities, the disabled individual may program the schedule for later use. For example, a disabled individual could program a schedule for Wednesday on Tuesday evening from the comfort of the individual's home. The schedule could be used during the ordinary daily chaos to help the individual get through expected changes in the daily activities. Likewise, the caregiver and the disabled individual may collaborate to create the schedule if desired.

Further, as described, the camera 24 and microphone 26 may be used to capture digital pictures, videos, and audio clips from the disable user's actual environment, such as the disabled user's actual school bus driver, bathroom sink, or playground known personally by the disabled individual. Such customized, dynamic, immersive creation of schedules represents one of many advantages. In many situations, children may more readily identify with known objects and persons than with stock images (though certain objects, such as a "police officer" the child has yet to encounter, may be better presented in generic form, else the child might be confused by a picture of a specific police officer whom is different than the one ultimately encountered). Further, such "actual environment" customization may in turn be used with respect to the visual countdown and choice offering functionality described below.

Figure 14:
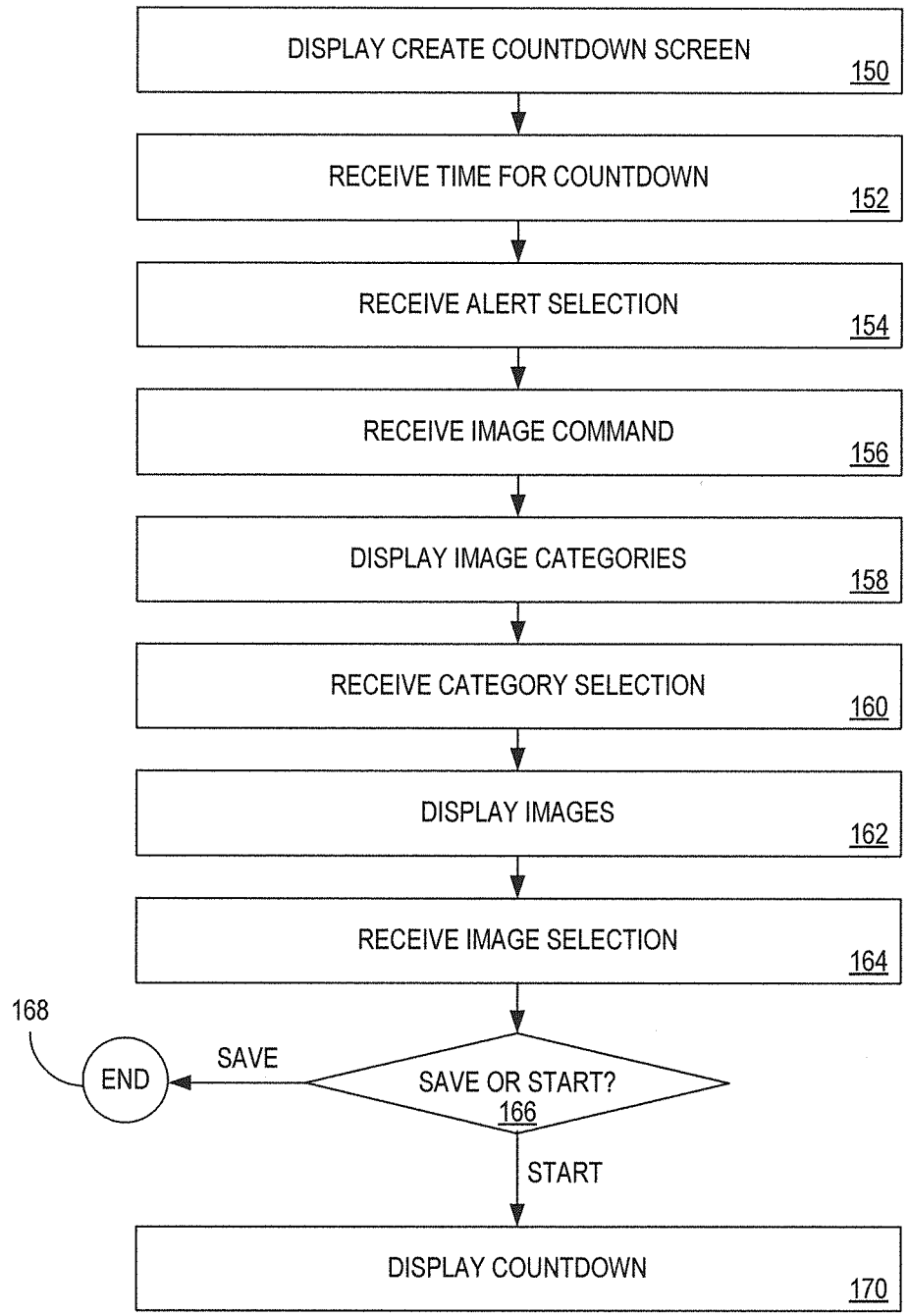
FIG. 14 illustrates a second flow chart showing a second portion of an exemplary embodiment of the present disclosure.
Figure 15:
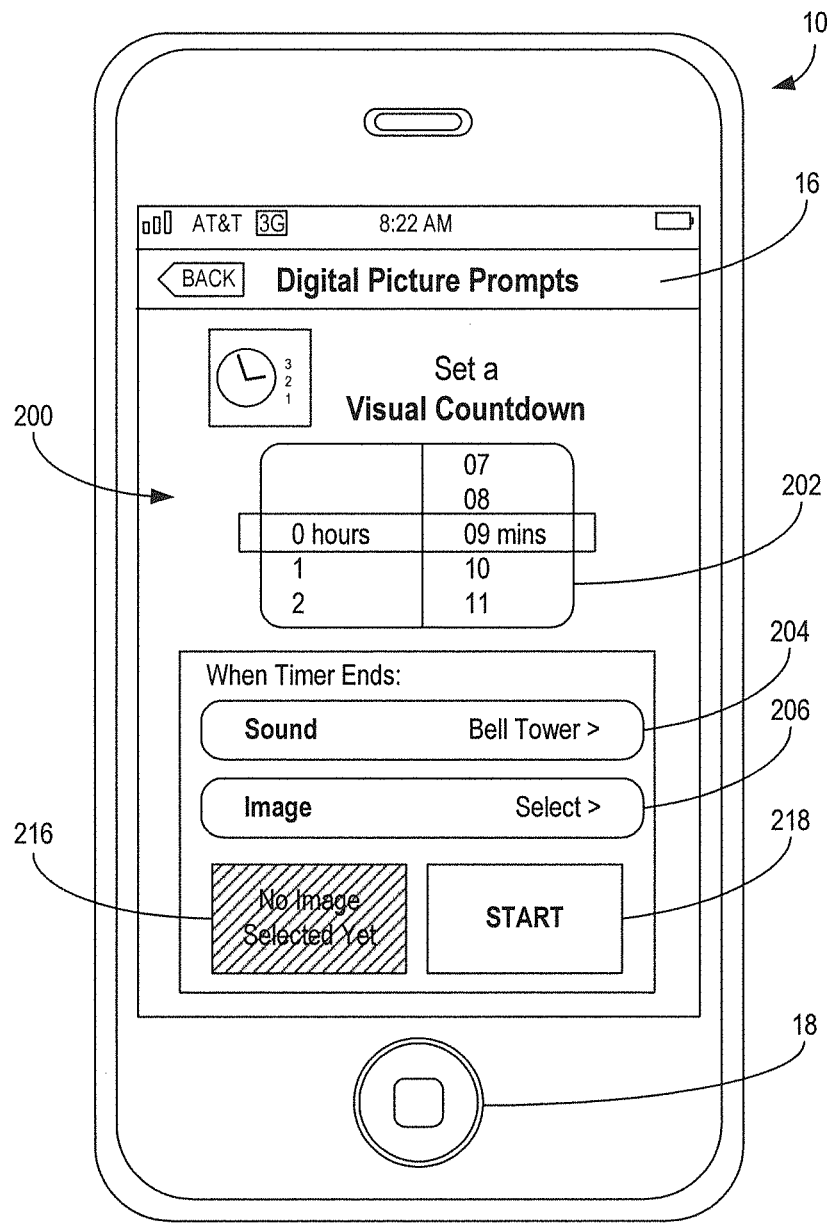
FIG. 15 illustrates a first screen shot associated with the flow chart of FIG. 14.
Figure 16:
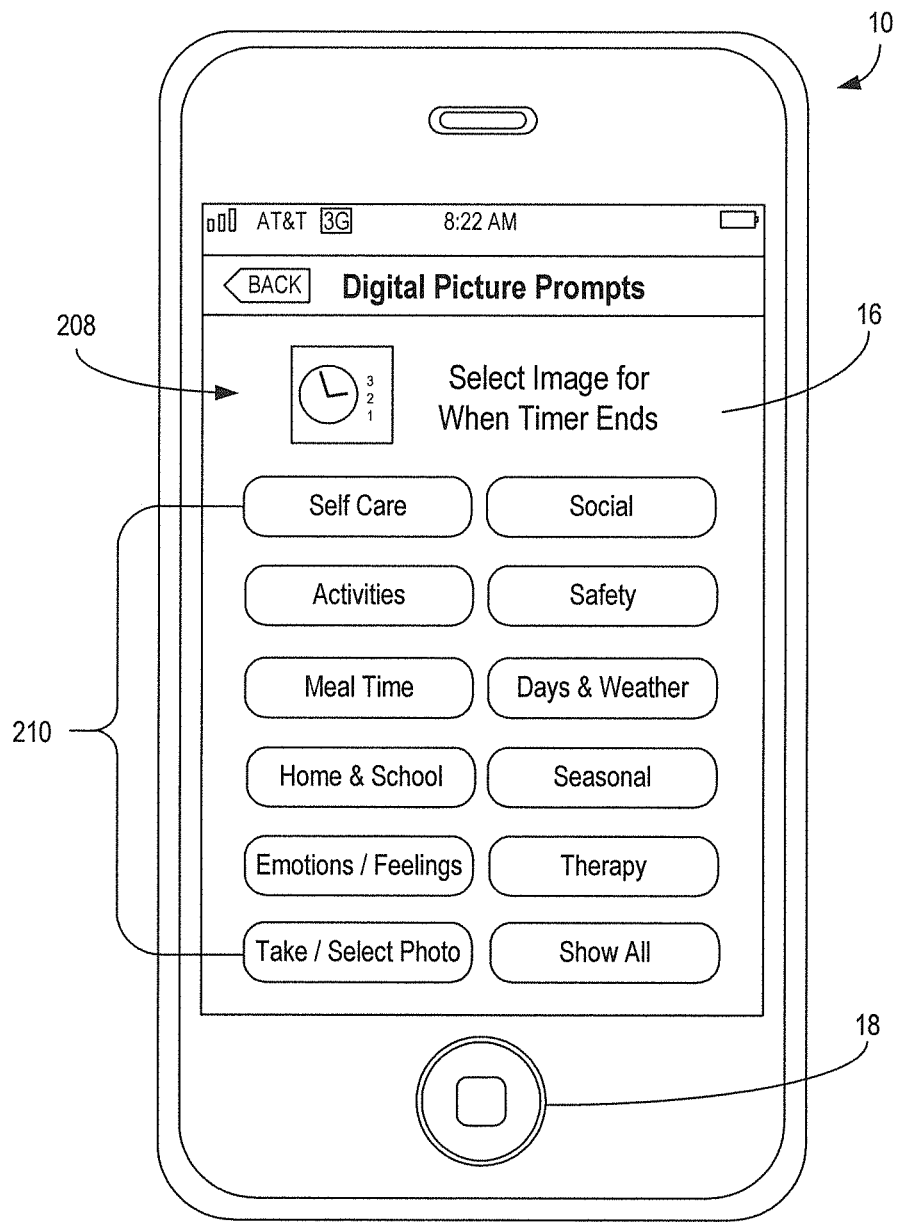
FIG. 16 illustrates a second screen shot associated with the flow chart of FIG. 14.
Figure 17:
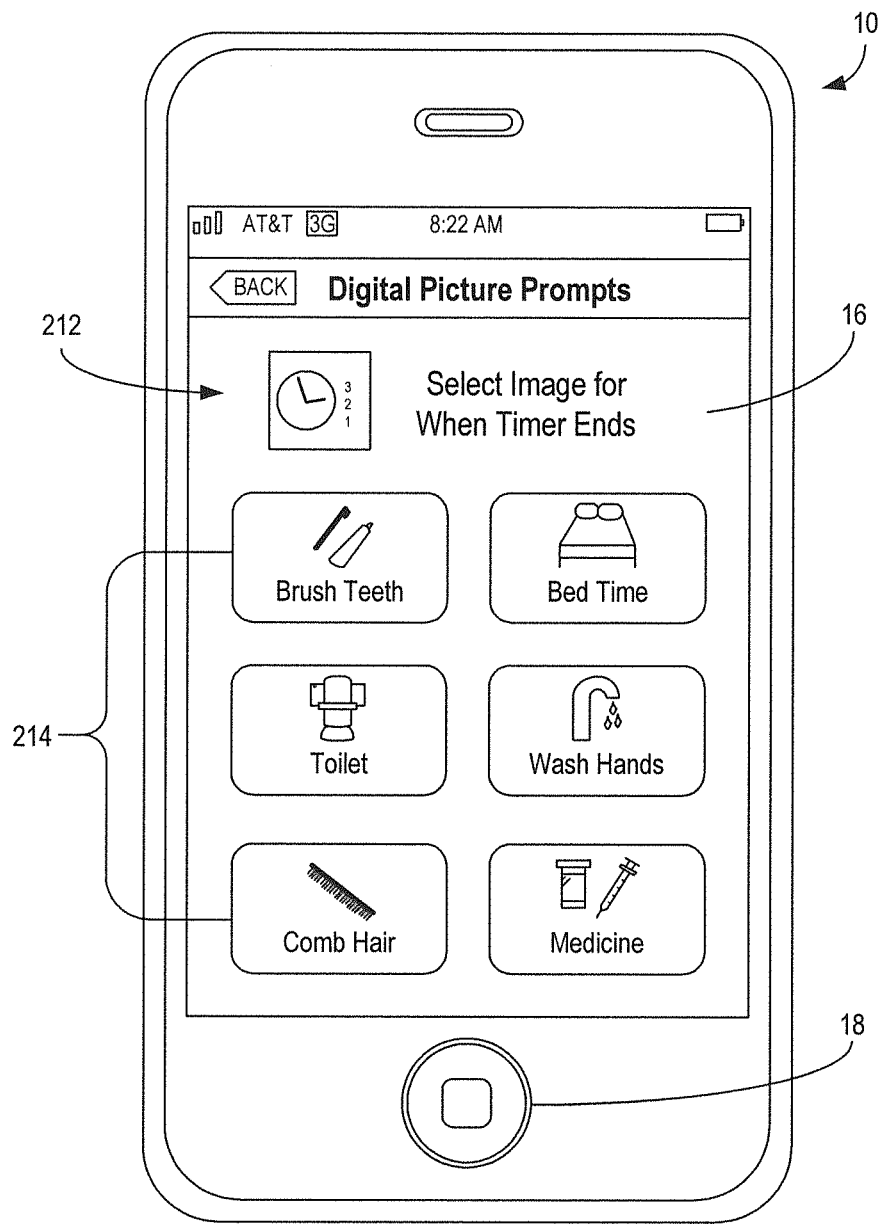
FIG. 17 illustrates a third screen shot associated with the flow chart of FIG. 14.

If the control system receives the set visual countdown selection at block 108 (FIG. 4), the process continues on as illustrated in FIG. 14. Initially, the control system displays a create countdown screen 200 (block 150) such as seen in FIG. 15. Note that the precise labels may be varied without departing from the spirit of the present disclosure (e.g., "set a visual countdown" may be replaced with "set timer" or the like). The control system receives a time for the countdown (block 152) such as by the user entering a time with the time entry button 202. The control system further receives an alert selection (block 154) such as through the alert command icon 204. The alert command icon 204 may include a drop down menu or other mechanism allowing the user to pick different sounds, images or videos as desired. The control system may further receive a select image command (block 156) such as when the user touches the image selection icon 206. Use of the image selection icon 206 may cause the screen to change to an image selection start screen 208 such as that illustrated in FIG. 16. The image selection start screen 208 may display one or more thematically-linked categories of image icons 210 (block 158). The user may select one of the icons 210 (block 160). The control system may then display the images associated with the selected image icon (block 162) such as with an image display screen 212 as illustrated in FIG. 17. The image display screen 212 may include a plurality of images 214 that are thematically linked to the selected category.

Figure 18:
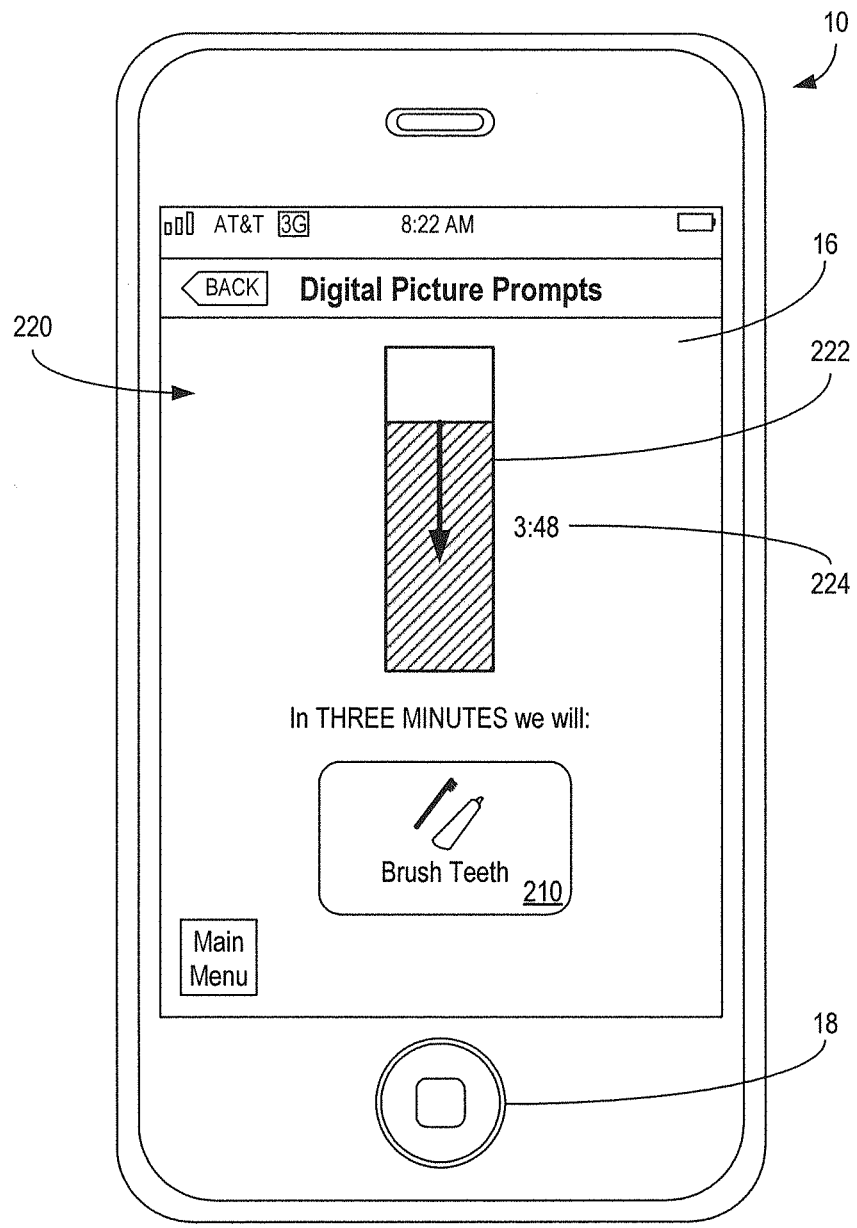
FIG. 18 illustrates a fourth screen shot associated with the flow chart of FIG. 14.

The user selects an image 214 (block 164) and the screen may return to the screen 200, but in place of the grayed out "no image selected" icon 216, the selected image may be displayed at the same spot. The user may be given the choice as to whether the user wishes to start the countdown timer or save it (block 166). If the user saves the timer, then the process ends (block 168) until the user recalls the timer and starts it. If the user starts the timer using the start icon 218, the control system may display the countdown (block 170) as illustrated in the countdown screen 220 of FIG. 18. The countdown screen 220 may include a graphical timer 222 (shown as a bar graph, but the graphical timer could take the form of an analog clock face, an hourglass, a train or car traveling down a track or road, a sun rising/setting, an animation which symbolizes a state of achievement or finality, or other representation), a digital countdown 224, and the image 210 selected when creating the countdown timer. While the countdown is in progress, the image may be "locked" such that the image cannot be changed. When the countdown has expired, the image may be unlocked and the user may change images for a future countdown. Note further a user may terminate a countdown before expiration if desired, such as through a "clear timer" command. When the countdown is exhausted, the alert previously selected may be generated. In an alternate embodiment, an image may be occluded by the timer, and as the timer exhausts itself, the image is revealed. Graphics and audio may also be utilized to inform users as the countdown approaches its conclusion (e.g., an alarm or beep at a halfway point, a one minute warning a screen flash occurring during the last few seconds, as a voice utters "3 . . . 2 . . . 1" via speaker 14, or the like).

Note that while not specifically illustrated, the screen shot of FIG. 9 could also include a command to add a countdown timer to the event so that the countdown timer previously explained may be used with events within the schedule. In effect, the process of FIG. 14 would become one more step within the process of creating the schedule. Also, though not specifically illustrated, countdown screen 220 might include an "add time" option. Selecting such an option could call up a separate screen or pop-up box to input an amount of time to add to the countdown. Alternatively, the user could simply select an "add one minute" option at the outset. Still another option would be to touch a declining progress bar and slide the bar up to add time. Time could be removed from the countdown in a similar fashion (e.g., slide the progress bar down to remove time or select a "subtract one minute" option). Such functionality would allow the caregiver to respond dynamically to ever-changing environments.

Figure 19:
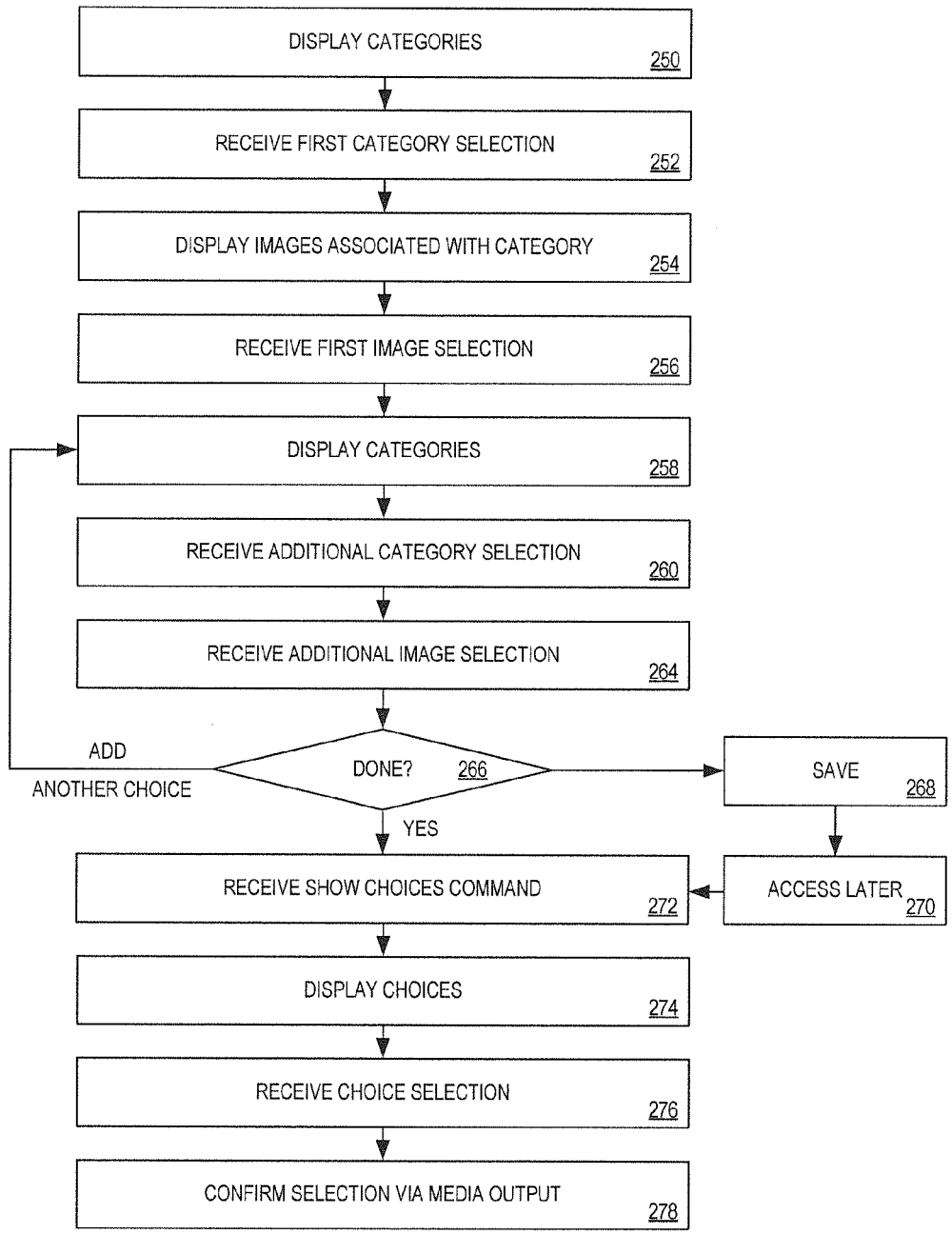
FIG. 19 illustrates a third flow chart showing a third portion of an exemplary embodiment of the present disclosure.
Figure 20:
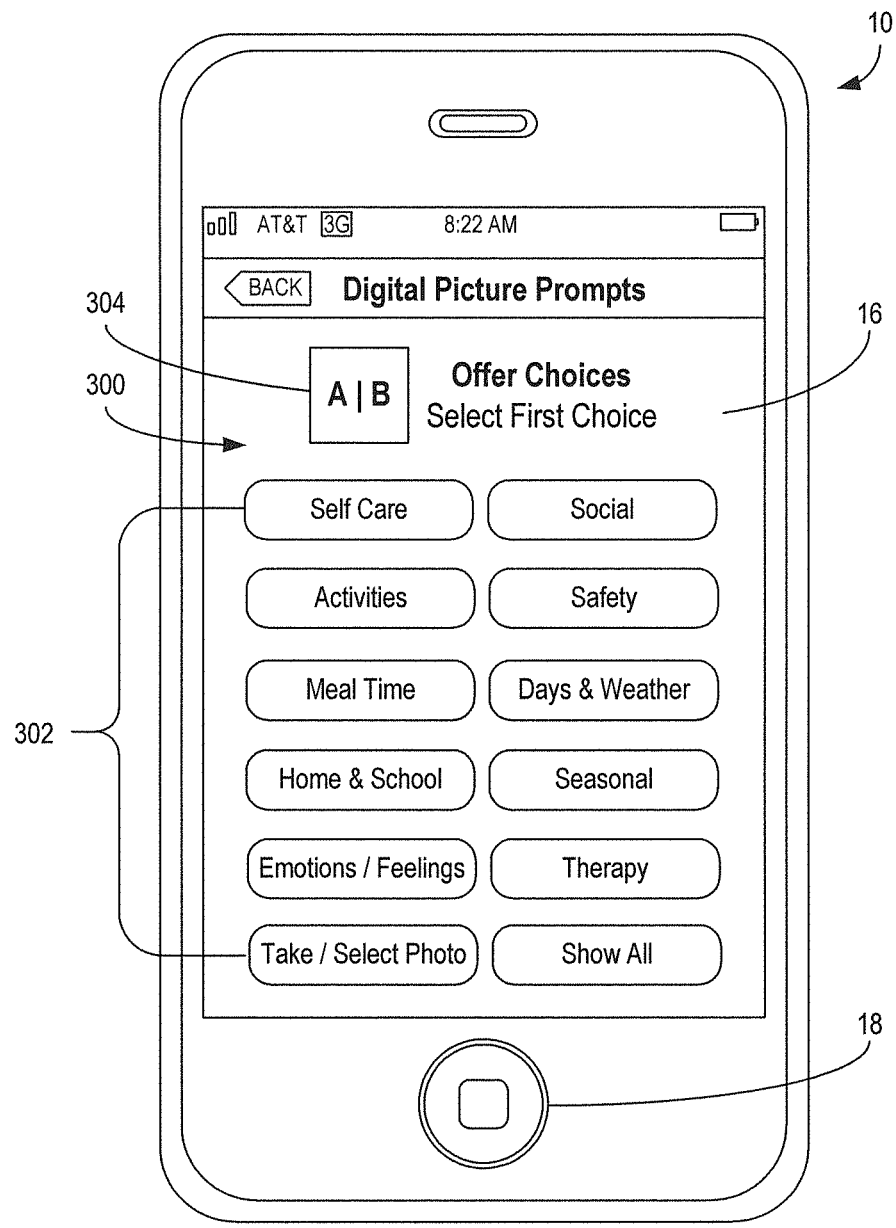
FIG. 20 illustrates a first screen shot associated with the flow chart of FIG. 19.
Figure 21:
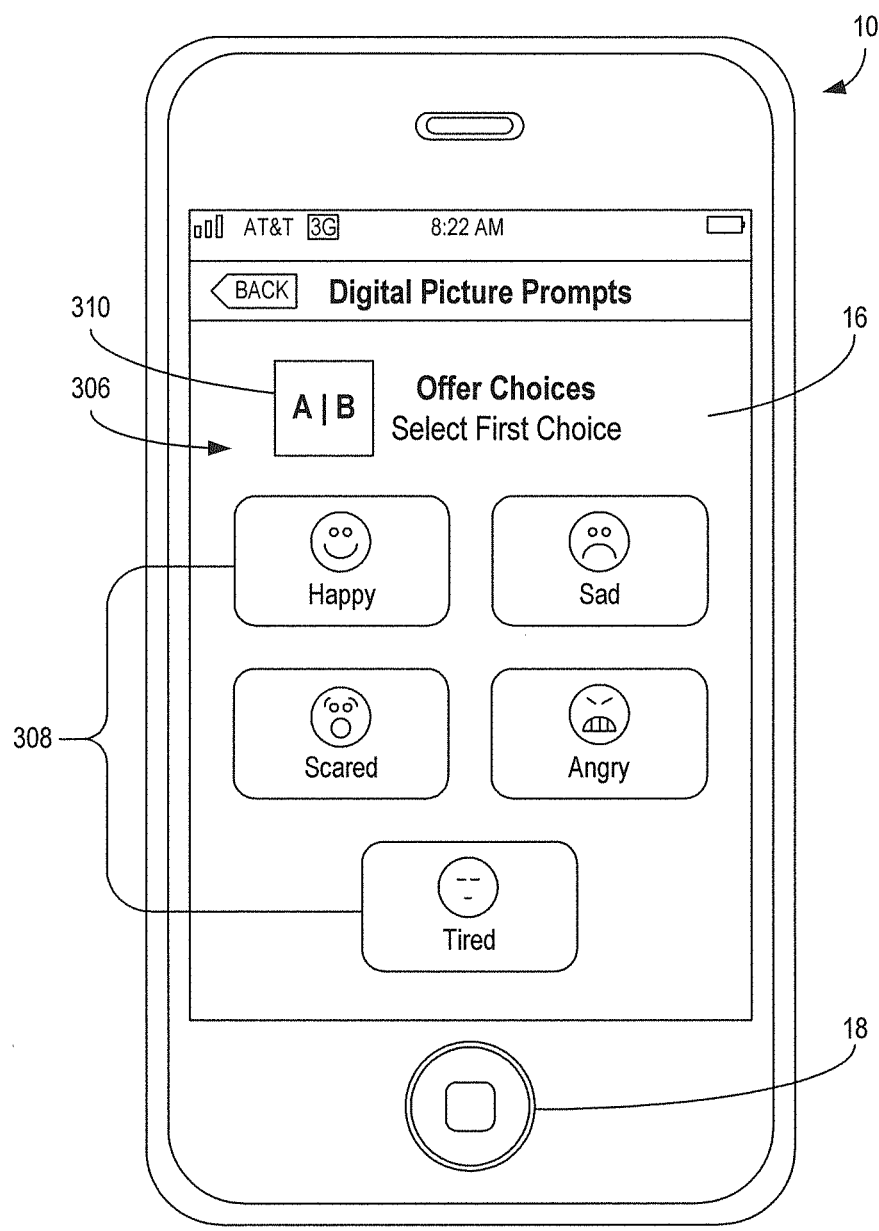
FIG. 21 illustrates a second screen shot associated with the flow chart of FIG. 19.

Returning to FIG. 4, the control system may receive an "offer choices selection" at block 110 if the user presses the offer choices icon 62. An exemplary flow chart of the process is presented in FIG. 19. After receipt of the offer choices selection, the control system can display the categories (block 250) such as illustrated by the screen shot 300 in FIG. 20. Category icons 302 are listed underneath a CHOICES heading 304. The control system receives a first category selection (block 252) and displays the images 308 associated with the selected category (block 254) such as through the screen shot 306 illustrated in FIG. 21. In particular, the images 308 may be displayed under instructional heading 310. The images correspond to one element from which a choice will be offered. Alternatively to the selection of a stored image, a user may elect to "take a photo now" using the camera 24. This "on the spot" image may then be presented as a choice, as described below.

Figure 22:
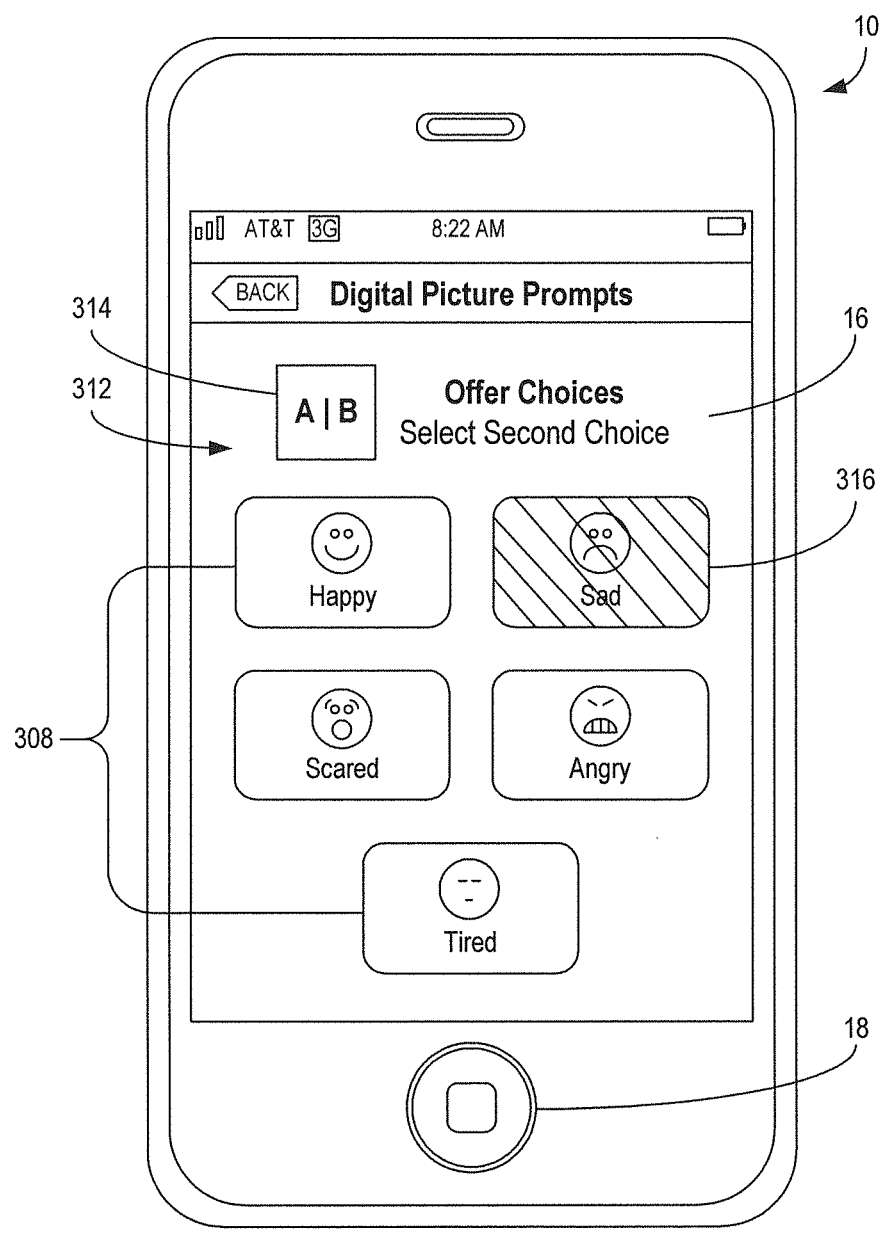
FIG. 22 illustrates a third screen shot associated with the flow chart of FIG. 19.

The user selects, and the control system receives a first image selection (block 256). The control system then displays the categories again for an alternate choice (block 258). This display is substantially similar to the screen shot 300, although the CHOICES heading 304 may be updated to reflect that this is the alternate choice. The user selects, and the control system receives the additional category selection (block 260). The control system displays the images 308 associated with the additional category such as through the screen shot 312 of FIG. 22. The images 308 may be displayed concurrently with the instructional heading 314. Note also that the image(s) that have previously been selected may be grayed out such as image 316 in FIG. 22. Alternatively, the previously selected image may just not be shown at this point.

Figure 23:
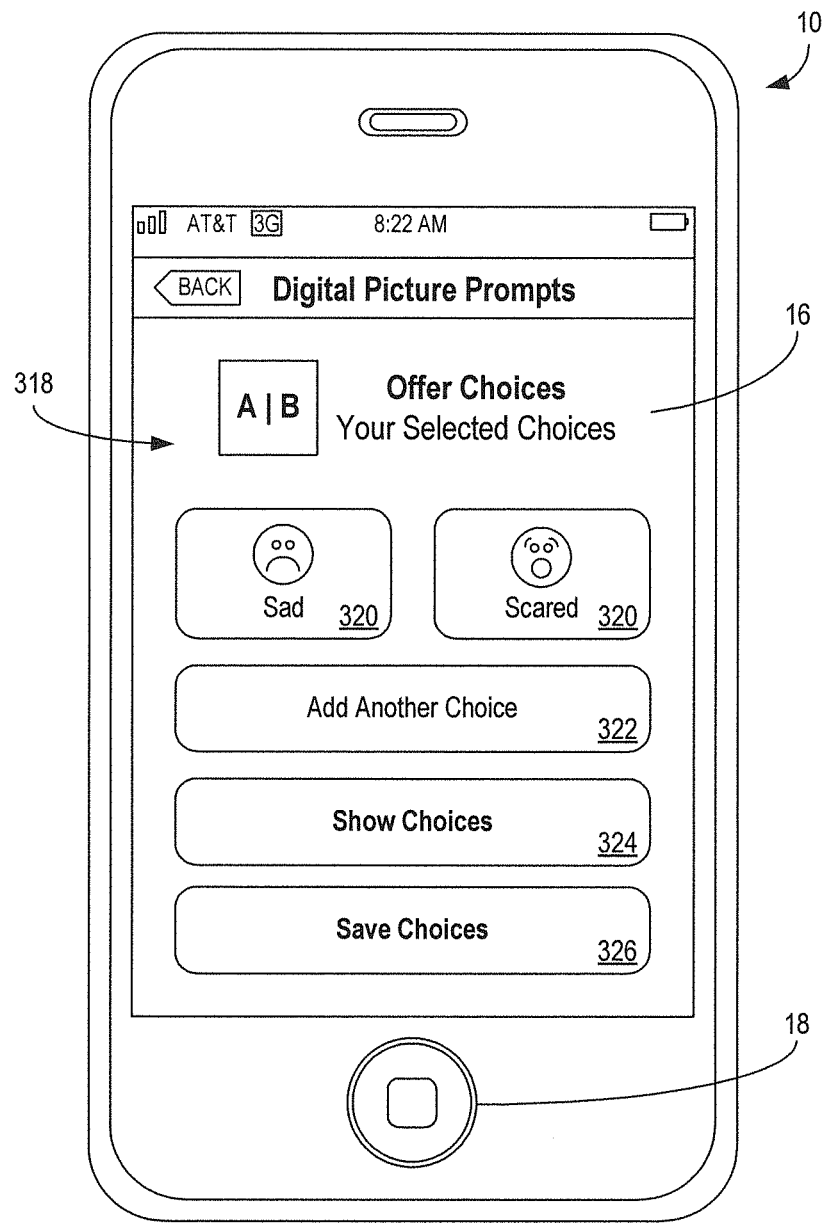
FIG. 23 illustrates a fourth screen shot associated with the flow chart of FIG. 19.

The user selects, and the control system receives the additional image selection (block 264). At this point, the control system displays an interrogatory about whether the user is finished with the choice selection (block 266) such as through screen shot 318 illustrated in FIG. 23. Images 320 from which the choice should be made are displayed along with icons for an add another choice option 322, show choice option 324, and save option 326. If the user selects add another choice, then the process repeats as noted in FIG. 19. If the user selects save, the choice is saved (block 268) until it is accessed later (block 270).

Figure 24:
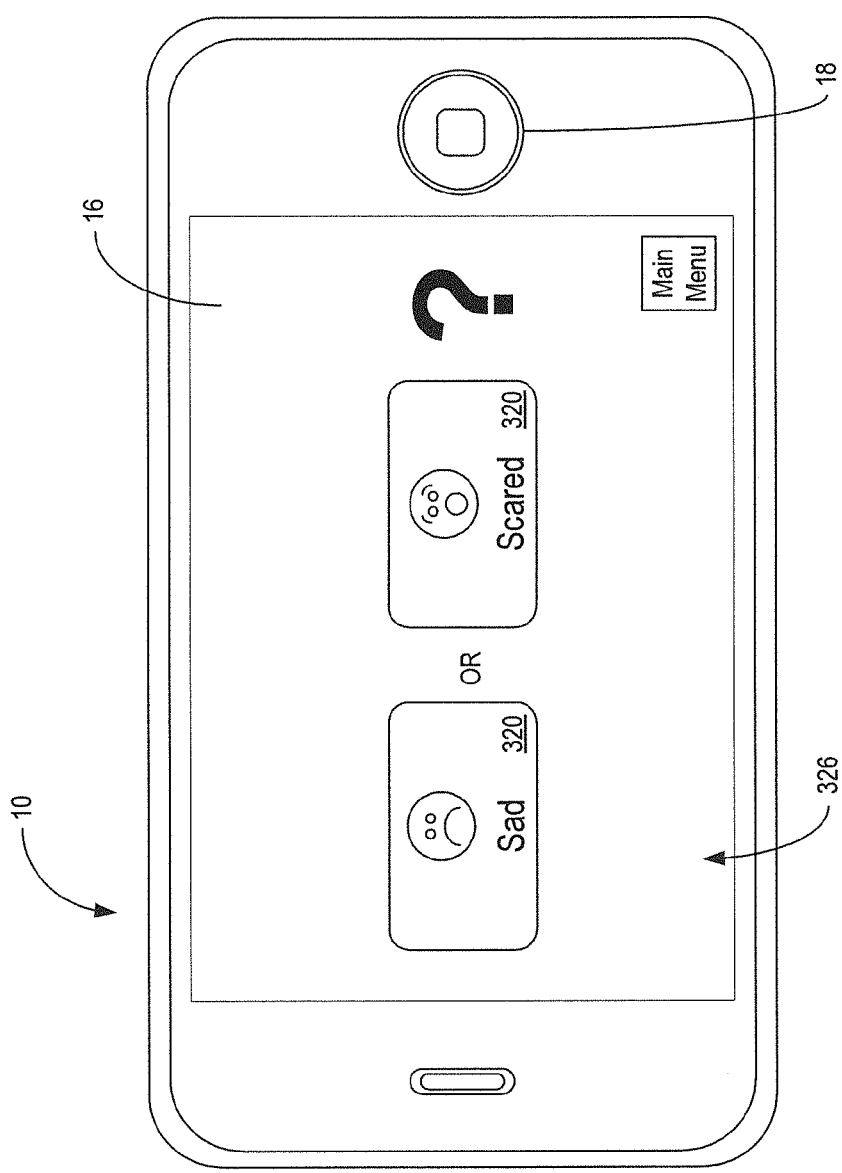
FIG. 24 illustrates a fifth screen shot associated with the flow chart of FIG. 19.
Figure 25:
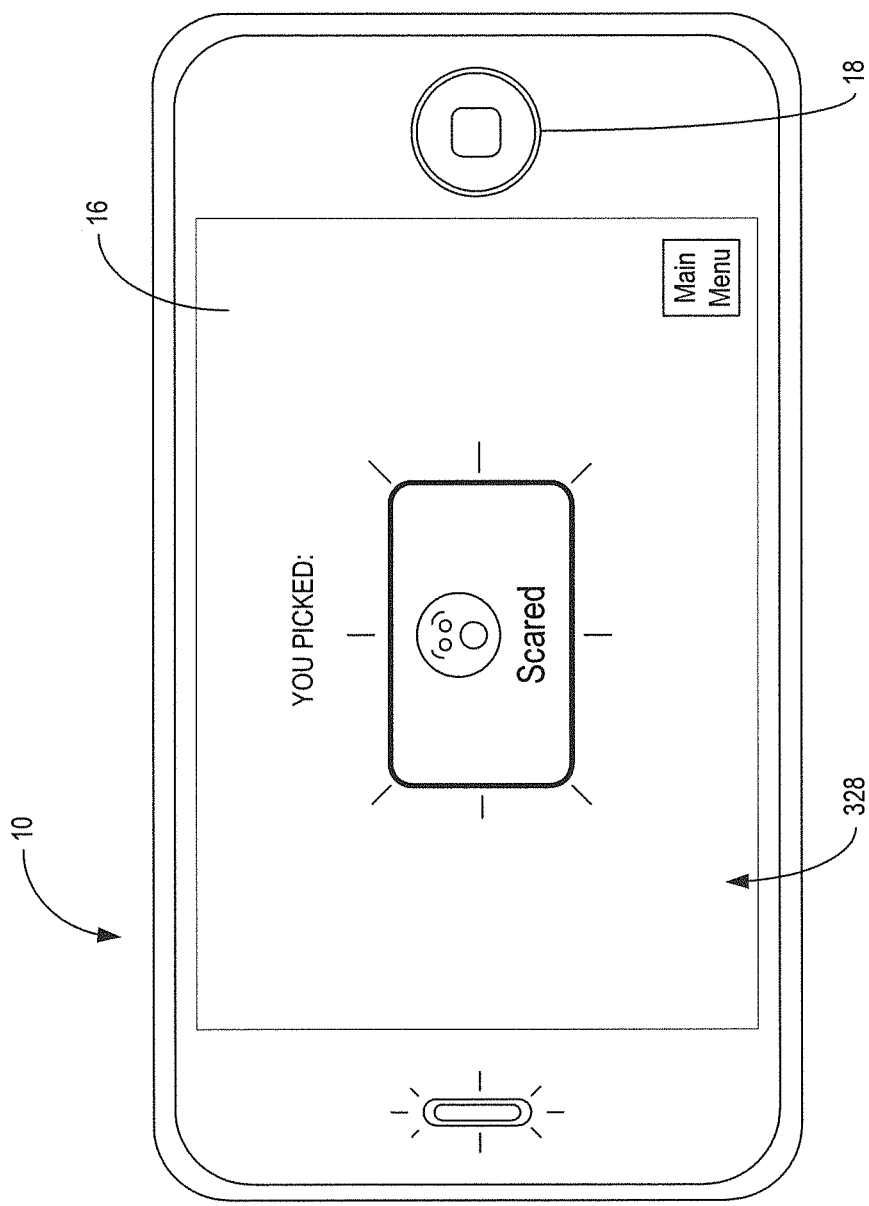
FIG. 25 illustrates a sixth screen shot associated with the flow chart of FIG. 19.

The control system receives the show choices command (block 272), either by the user accessing a saved choice or by selection of the choice option 324. The control system displays the choices (block 274) such as through screen shot 326 illustrated in FIG. 24. The control system receives the choice selection (block 276) such as through the disabled individual pressing the desired one of the selected images 320. The control system may then output a confirmation (block 278) such as confirmation screen shot 328 illustrated in FIG. 25. Graphical enhancements or animations such as highlighting, flashing, or the like may be output at this time (e.g., a border around a selected image flashes). Other media, such as audio or video, may also be used to indicate such selection confirmations (e.g., "you chose ice cream"), thereby responding to the disabled individual's selection of a nonverbal prompt with a verbal reinforcement, which would serve to teach and encourage speech and language development.

As should be readily appreciated, the choice selection allows the caregiver to give a nonverbal disabled individual a graphical option to express themselves. This may be especially useful in ascertaining an emotional state of a child and helping the caregiver to understand what the disabled individual needs or wants. Further, the dynamic, rapid assembly of choice options based on changing environments makes for a richer, more valuable tool. Pictures of the actual disabled individual in certain moods or environments (e.g., a picture of the actual child crying) may be used as images 320, according to the aforementioned benefits of personalization.

The methods described above lend themselves to databases of images. An exemplary image database 350 is illustrated in FIG. 26. The database may include fields such as image name 352, category 354, used in schedule 356, used in countdown 358, and used in choice 360. The name may include the file name and/or the location in which the image file is stored. It is contemplated that the images may be digital pictures, drawings, illustrations, or the like. Likewise, while described throughout the examples as still images (e.g., files stored in .jpg, .gif, .bmp, or the like format), it should be appreciated that video images could also be used as desired. The category 354 may list what thematically-linked categories with which the image is associated. The used in schedule 356, used in countdown 358, and used in choice 360 may list any saved files of the appropriate type in which the image is currently used. While not shown in the database 350, the images may include metatag information. This metatag information may be provided by the original image provider, added by the caregiver, or the like (e.g., each image includes an editable title and several editable metatags). This metatag information may be alphanumeric and may accordingly facilitate keyword searching to make use of the embodiments described herein more convenient. Alternatively or additionally, the metatag information may be in the form of an audio file, such as a voice file, so that images may be searched and/or retrieved from the database based on an audible input received from a user through microphone 26 and interpreted through speech recognition software. Still another option would be to allow the metadata to invoke alternate functions within the mobile terminal 10. For example, a buzz or vibrate command could be embedded in the metadata such that when the image is shown in a schedule, the mobile terminal 10 vibrates. Extending the example, a photograph of a hair clipper has metadata that causes the mobile terminal 10 to activate its vibration unit. The caregiver incorporates the image of the clippers into a schedule and when the schedule shows the clippers, the mobile terminal 10 vibrates for the disabled individual. This functionality may help prepare the disabled individual for sensations that may be experienced.

Figure 27:
FIG. 27 illustrates a second exemplary database suitable for use with the present disclosure.

In addition to the image database 350, a saved file database 361 may exist and is illustrated in FIG. 27. The database may include fields such as file name 362, images 364, timer 366, times 368, and type 370. The file name may be the name the user gave the file when it was saved. The images 362 may list any images or image locations, or pointers to images used by the file. If there are timers associated with an image, the timer may be listed in timer 366. If an activity or file is to be used at a particular time, that fact may be stored in the times field 368. A program like MICROSOFT OUTLOOK™ may integrate with the database 361 and use times in the times field 368 to note events in the calendar program. Likewise, such a program, when the time is nigh could launch the appropriate schedule, timer, or choice. Otherwise, the system clock could be used to launch the appropriate schedule, timer, or choice. The type field 370 may indicate whether the file is a schedule, timer, or choice file.

In an exemplary embodiment, images may be stored with the software on purchase. Additionally, users may use the camera 24 of the mobile terminal 10 to capture images and use with the methods described herein. The use of custom images in this manner may be particularly effective for particular environments or events. For example, a picture of a particular community pool may be more effective at communicating the concept of going to the pool to a particular disabled individual than a pencil drawing of a generic pool. Likewise, video images may be used in this manner to communicate more effectively in certain instances. Thus, a video with audio of children splashing around and the usual activities of a particular community pool may be more effective at communicating the concept of going to the pool than a pencil drawing of a generic pool.

Still further, a central server accessible through the internet might host updates to the software including additional images, videos, or the like. The updates could be downloaded to the computer 54 and then passed to the mobile terminal 10 or accessed through the PLMN. Likewise, images (or entire schedules) could be shared between caregivers on a peer-to-peer network, file share lists, via email, or the like. Caregivers could share images from mobile device to mobile device via BLUETOOTH™ or another protocol.

Additionally, the schedules, timers, and choices do not have to be created on the mobile terminal 10. Rather, in some embodiments, the files may be created on the computer 54 and uploaded through any of the various networks to the mobile terminal 10. This arrangement also allows photos, images, and video from sources other than the camera 24 to be used with the software described herein. Instead of hosting just updates, a server could support thin client versions of the software wherein images, audio files, videos, schedules, and the like are all stored on the central server and then downloaded or streamed to the mobile terminal 10 as needed or used. Schedules and/or other elements could be uploaded to the server and subsequently shared amongst users (e.g., one parent uploads a "Bronx Zoo" schedule including captured images, audio, and video, such that a second parent can download the schedule and prepare his or her child for an upcoming trip).

Social networking functionality such as the ability to create and manage a "friends" list, or the like, could further be used to share elements. Such functionality may be provided by a web site, or through software stored on the mobile terminal 10. Content sorting or categorization features such as "most recent", "most popular", or the like may be provided, allowing users to find schedules, images or other media files they desire efficiently. Buttons may be provided to allow images, schedules and the like to be added to a "my folder" automatically.

In one embodiment, a registration sequence fee may be required to access a central database of content, access the social networking site, receive software updates, or the like. For example, a user may be required to provide contact information and configure a login and password to access such content. In one embodiment, users may be charged a subscription fee to access a central database, social networking functionality, content sharing functionality, and/or receive software updates.

Many mobile terminals are becoming more adept at voice recognition. Various elements of the present disclosure may be facilitated or alternately implemented to take advantage of these advances. For example, the images may be tagged for retrieval using voice recognition. Likewise, when creating schedules, timers, or choices, the data entry may be effectuated through voice recognition software rather than the touch screen example used above. Still further, the mobile terminal 10 may be trained to recognize a disabled individual's non-lexicographically recognizable utterances as particular inputs. Such may be particularly appropriate for the disabled individual to select a choice.

While the discussion is presented as if all images can be sorted into one or more categories, it is also possible to arrange the images with sub-categories and the like. Likewise, there is no requirement that an image be limited to a single category or sub-category. In one example, a speech therapist may create categories and/or sub-categories of images, saved schedules, saved timers and/or saved choice prompts which are customized for individual therapy clients.

Note further, that schedules, choices and timers may be shared between caregivers through any suitable network.

Note further that while audio alarms were discussed above in terms of pre-generated sounds, the audio alarm could be a recording of the caregiver providing instructions. For example, on the expiration of a timer, the caregiver could be heard to say "all done watching TV, time to brush your teeth." Likewise, proximity alerts may be provided such as "two more minutes of TV, then it will be time to brush your teeth."

Recordings may also be used at other events such as a choice offered to a disabled individual. When the disabled individual makes a choice, the speaker may play the recording of the caregiver saying "You chose scared" in hopes that the audible repetition may assist the disabled individual in acquiring this language into their vocabulary. In still another embodiment, a video may be provided of the caregiver making such a statement or modeling the proper mouth movements to assist the disabled individual in learning how to produce the sounds necessary to speak the word associated with the selected choice. Such recordings may be captured using the mobile terminal 10 or using a personal computer (with subsequent transfer to the mobile terminal 10).

ALTERNATE AND ADDITIONAL EMBODIMENTS

Alternate Triggers

Many of the above examples have focused on the use of the clock or a timer to cause a particular image to be shown to the disabled individual, but the present disclosure is not so limited. Location or other environmental activity may act as a trigger. In an exemplary embodiment, block 126 (FIG. 4) and the set event time icon 76 (FIG. 9) may be replaced with more generic commands. For example, the set event time icon 76 could be replaced with "set event trigger" and block 126 could be replaced with "receive command to set event trigger". Exemplary triggers are geographic location and/or direction of travel, vibration or agitated motion detected by the accelerometer, volume levels detected by the microphone exceeding a predefined decibel threshold, a level of brightness detected by a light sensor, detection of specific verbalizations on the part of the disabled individual (e.g., the disabled individual says "cross street" and a cross street schedule launches (e.g., an image of eyes with a left arrow, an image of eyes with a right arrow, a car with a red X superimposed, an image of the disabled person crossing a clear street holding hands with a caregiver, or the like), heat detection by a thermometer, consultation of an external weather website to see if rain or other inclement weather is expected, updates from an RSS feed (e.g., weather, grocery alerts (e.g., Stop N Shop has KRAFT® Macaroni & Cheese on sale for $0.49/box, buy now), or the like), or the like.

Further, instead of launching specific schedules, choices or a countdown timer could be triggered based on such alternate triggers. Further still, while such triggers may be set by a user, triggers may alternatively or additionally be determined by the device inferentially based on data available to it and/or according to stored rules, including as described further herein.

Further still, instead of a particular application launching based on a particular trigger, a palette for creating a schedule, countdown timer or choice may be determined by the device and output for consideration and use by a user based on one or more triggers. A palette may be a subset of all images, videos and other media available to the device, where the subset is determined to be relevant or potentially relevant to a given situation based on one or more data points available to the device (e.g., through sensors and databases). For example, if the device were to determine that the current day is a Tuesday in February (based on a calendar function and built in clock), the GPS coordinates indicate that the device is in a certain region, and a weather database (either local or external to the device) indicates that snow is likely, the device may create a palette of images for use in a schedule, countdown timer or choice prompt including images such as snow boots, a shovel, a plow truck, a wool hat, and the like. The subset may then be used to help a caregiver or disabled user create situationally-relevant schedules, countdown timers or choice prompts more efficiently as compared to doing so by manually searching a broader library which may include many images and/or other media that are not particularly relevant for the given context. In other words, the device may proactively suggest relevant palettes of images or other media from which the user can readily construct schedules, countdown timers or choices.

Thus, in alternate embodiments, sounds, images, or videos may be recalled from memory 30 and queued for output in a visual countdown feature based on one or more data points available to the mobile device 10. For example, if, based on a GPS sensor and associated mapping software, the device can determine that, at the current rate of speed, the device will be transported to a given location by a certain time (e.g., in 30 seconds based on the current rate of travel, directional trajectory, and map data, the device will be carried over a bridge), then the device may queue associated sounds, images, or videos for use in a countdown timer application (e.g., an image of a bridge). In this way, the countdown timer may "adapt" to the situation by inferentially anticipating sensory stimuli (e.g., visual, auditory) that will be or is likely to be in a disabled individual's environment in the near future. The device may then display an appropriate visual countdown timer where the time is set based on the anticipated time until the anticipated sensory stimuli will be present. The queued sounds, images, or videos may be selected based on (i) the anticipated sensory stimuli and/or (ii) a particular user's sensory preferences and aversions (as recorded in a database). In this manner, the present disclosure provides an "early warning" of sensory stimuli for individuals with sensory processing dysfunction. Further, in yet other related embodiments, the device may record and analyze a particular disabled individual's reaction to certain sensory stimuli so that it can queue up appropriate sounds, images and videos based on what appears to bother or cause anxiety for the individual. For example, the device may be programmed to trigger, based on a sensor such as a thermometer, heart rate monitor, pressure sensor, microphone, camera and/or GPS that the user is reacting negatively to certain sensory stimuli then present in the environment. For example, if the disabled user's heart rate has increased and/or skin temperature has increased, and/or if the disabled user has screamed or otherwise loudly exhibited distaste for the given sensory situation (e.g., as detected by the microphone as being above a certain decibel threshold), the device may then record data pertaining to the surrounding circumstances (e.g. take a picture, record the GPS location, record audio, etc.) so that at a later time when the same situation is anticipated (based on GPS, based on an entry in an on-board calendar), the recorded data may be incorporated into a visual (or audio-based or "multisensory") countdown timer (and/or a graphical schedule).

In still another alternate embodiment, the user may be able to advance manually a schedule of events. Such might be useful when routine tasks are being performed with no particular time frame required (e.g., for a "getting dressed" schedule, the user may advance manually through underwear, socks, pants, shirt, shoes, comb hair rather than have a particular time set for each task).

Software Adjustments Based on Environmental and Use Inferences

In addition to schedules and the like created by the caregiver, and as alluded to above in the alternate trigger section, the mobile terminal may infer potential schedules or events. Such inferences may be drawn from another application, computer, device peripheral or sensor (e.g., a GPS receiver). For example, if for four days in a row the mobile terminal is conveyed to a pool at 2 PM, the device may infer based on the clock and output from the GPS receiver that on the fifth day they are also going to the pool. A countdown may be provided as the device nears the pool. Alternatively, if the weather report pulled from an RSS feed indicates a hot day, a palette of images associated with heat may be provided to the caregiver when the caregiver uses the software of the present disclosure. Still other data points may be taken from a calendar function. For example, if the calendar indicates physical therapy, the control system may pull up images tagged with a physical therapy metatag.

Still another inference may be the level of abstraction used in the images. More detail may be provided if the microphone detects noise above a certain decibel threshold, a pressure sensor senses the mobile terminal 10 being squeezed or thrown, a thermometer detects a change in body temperature or the like. Less granularity may be provided if the disabled individual is advancing through events quickly and/or the device is passing through physical space quickly (per GPS or other sensors available to it) and/or if there are more than a threshold number of events in a given schedule (where the user can then select the more abstract image used as a substitute if more granularity is ultimately desired or needed). For example, instead of showing sequential images of socks, pants, shoes, and the like, the image may just be an image for "getting dressed" (and the user could later select the more generic image to see the individual, specific images of socks, pants, shoes, etc.).

Still another inference may be an "auto-save" or "suggestion to save" feature. For example, if a caregiver repeatedly (e.g., twice or more) configures and presents a choice between two specific options, the set of choices may be automatically saved on the user's behalf (and perhaps labeled with the time and date of creation), or the user may be prompted with a suggestion to save the set of choices (e.g., "Would you like to save 'Play with Cat' versus 'Play with Dog'?").

Speech to Image Reinforcement

In yet further alternate or additional embodiments, the disabled individual may be prompted via an audio recording to speak a word or words associated with the selected visual choice. For example, if the disabled individual selects an image of ice cream, the device may then output through speaker 14 a recorded prompt such as "say 'Ice Cream'", thereby encouraging an individual with verbal communication challenges to practice their verbal utterances and requesting skills. Further still, the device may be configured to employ microphone 26 and associated speech recognition or audio file comparison software to record and analyze any auditory utterances provided by the disabled individual such as by (a) recording an audio file of an utterance in association with the particular image so that when the device later detects the individual making the same utterance or a substantially similar utterance, it can recall the associated image and thereby "translate" the received utterance to a caregiver by outputting on the display 16 the image(s) associated with the (perhaps otherwise unintelligible or poorly articulated) oral utterance, and/or (b) prompting the individual for a refined or prolonged utterance (e.g., "now say 'I want Ice Cream Please.'"), which would serve to help improve and encourage better verbal articulation, sentence construction, mean length of utterance (or "MLU") and socially appropriate courtesies and manners. In this manner, the device may "adapt" to the individual, and the individual may be encouraged to "adapt" to the (social) environment. In addition, or as an alternative, each image may have a "press-and-play" associated audio file. These associated audio files may be linked into the schedules, countdowns, or choices automatically or at the discretion of the user. When a user touches the image, the audio file may play. For example, an image of a slice of cake may be linked to a recording saying "cake". Like the customized images, these audio files may also be customized. For example, the picture of the family dog may be linked to a recorded bark of the family dog or the disabled individual's parent saying "Fido" or the like.

Alternate Navigation

Figure 28:
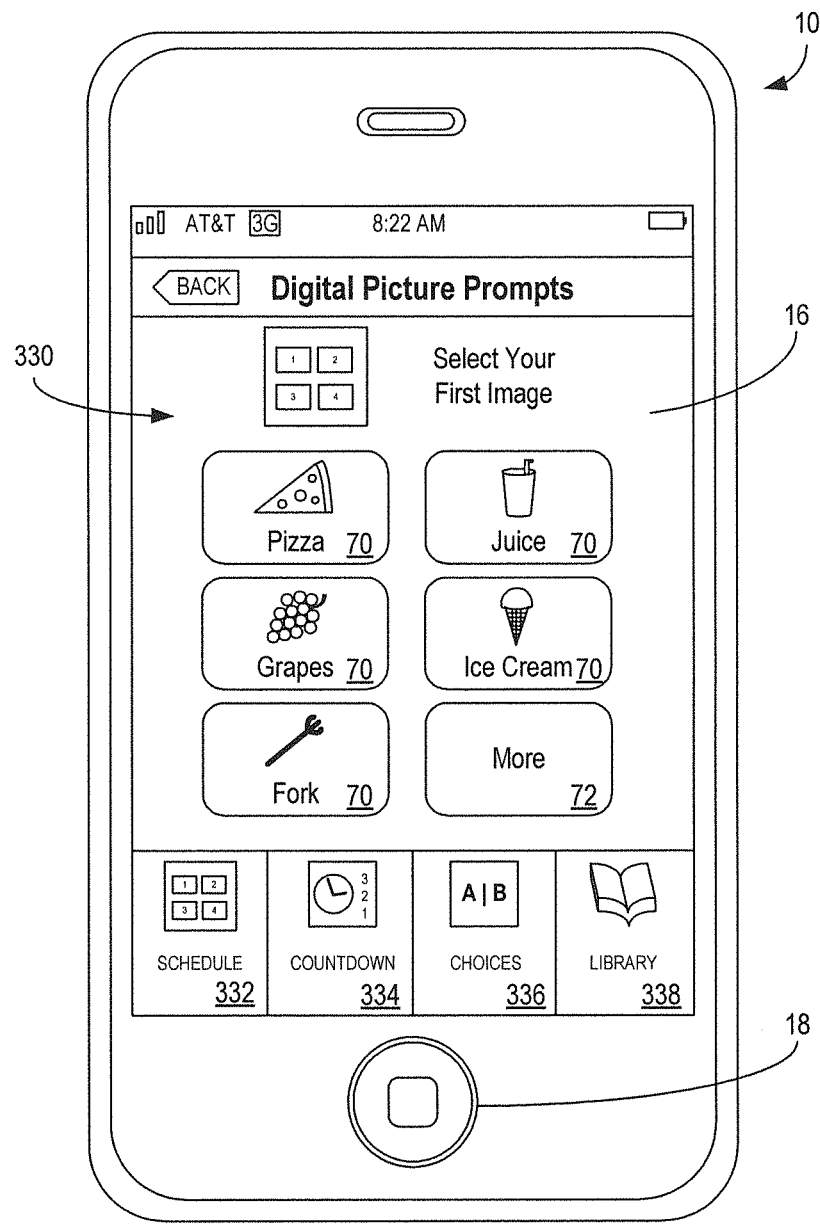
FIG. 28 illustrates a screen shot associated with an alternate embodiment of the present disclosure.

Various screen shots and flow charts have been provided in an effort to illustrate some navigational possibilities provided to users of the software described herein. It should be noted, however, that these navigational organizations are examples, and that others may be utilized without departing from the spirit and scope of the present disclosure. As an example, an alternate organization is depicted by the screen shot 330 of FIG. 28. While the processes for utilizing image schedule, countdown timer and choice applications may remain similar, screen shot 330 depicts an interface whereby users can select tabs 332-338 to access such applications. These tabs may persist across the bottom of display 16. For example, as is shown by screen shot 330, the user is "in the middle" of creating a picture schedule, though the user may select tab 332 to "start again" and create a new schedule, tab 334 to advance directly to the countdown timer application, tab 336 to advance directly to the choice offering application, and tab 338 to advance directly to the library.

Should the user indeed select tab 338, a library interface (not shown) may allow the user to access and edit stored media. For example, the user might browse a list of stored images (stock images, "my photos," etc.), and edit the titles or captions associated with each image.

Further Schedule-Based Interactivity and Games

Figure 12:
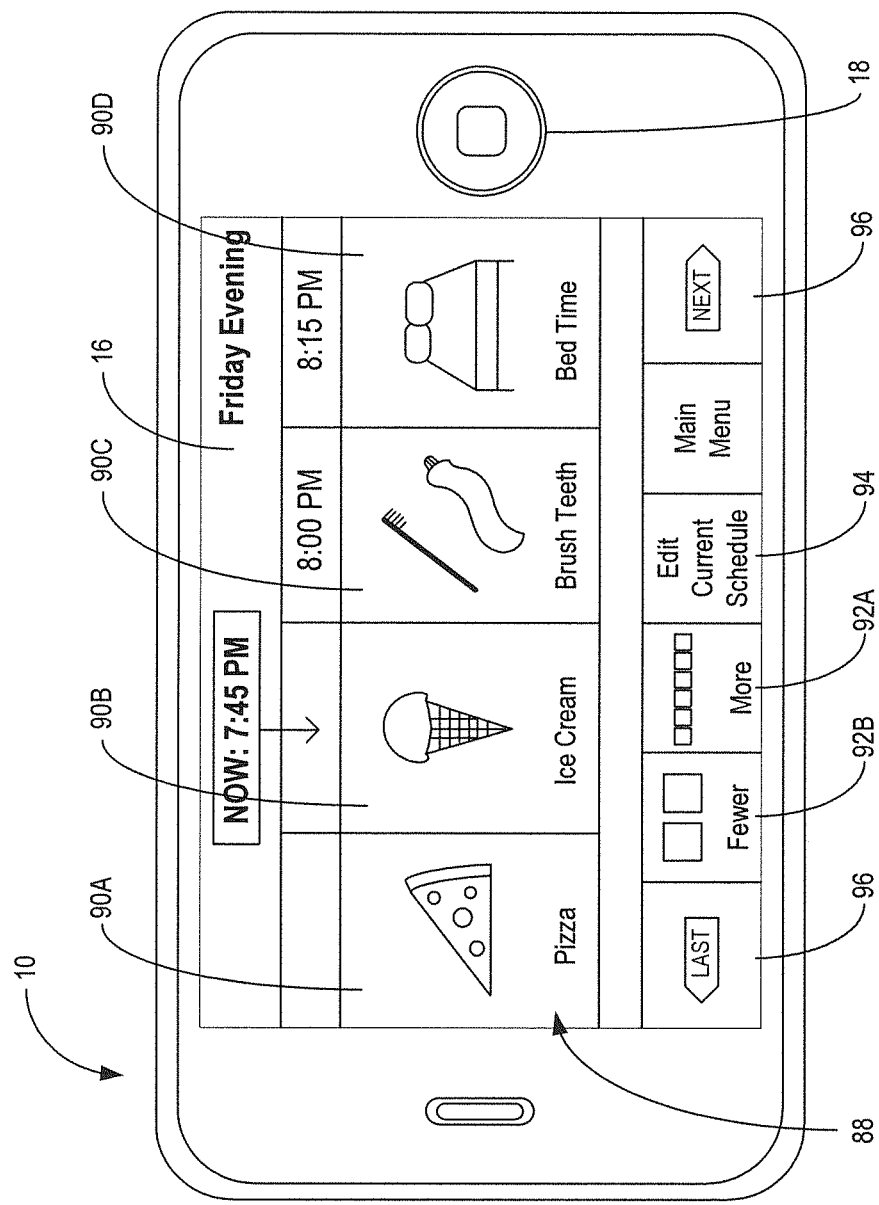
FIG. 12 illustrates an eighth screen shot associated with the flow chart of FIG. 4.

During the presentation of a schedule, such as the schedule shown by screen shot 88 of FIG. 12, an option (not shown) may additionally be presented to play a game or answer a question based on the schedule in use. For example, again referring to screen shot 88, the disabled individual might be asked, "What comes next?" Such a question might be presented via display 16 and/or speaker 14. Based on the current time of 7:45 p.m., the correct answer would be "Brush Teeth"; accordingly, this image and other images may be utilized in a multiple choice format. The disabled individual would use means described herein to select an answer choice. Correct and/or incorrect responses may then be confirmed to the disabled individual via the display 16, speaker 14 and/or the vibration unit. Other questions might be presented in the format of "What comes after (current activity)?" or "What comes before (future activity)?". A caregiver may select the option (not shown) to present such questions to the disabled individual, or the disabled individual may proactively select the option. In a further embodiment, incorrect answer choices selected by the disabled individual may result in the automatic presentation of a choice between the incorrect answer and the correct answer ("story time" is next on the schedule, though the disabled individual selected a "play with dog" image instead, so the disabled individual is presented with a clear, binary choice between the two to confirm the disabled individual's desire). In alternate non-mutually exclusive embodiment, correct responses may be awarded with some form of graphical reward (e.g., a coin, token, points, stars, or the like). Rewards may also be extended to completing elements within a schedule at an appointed time or obeying the time allocated by a countdown timer. These rewards may be stored in a profile associated with the disabled individual, and a caregiver may later allocate a tangible reward. E.g., "Jimmy got six stars today so he can have two scoops of ice cream instead of one."

Reporting and Usage Notifications

Usage statistics may be kept for various purposes. In one example, as described above, repeated configurations may be automatically saved on the caregiver's behalf. In another example, usage data may be stored internally on the mobile device and later transmitted, via a computer 54, to caregivers, to software manufacturers and even to medical research communities. Such data may help inform of usage patterns, potentially giving rise to further diagnoses associated with specific disabled individuals, academic usage of aggregated statistics, and further utilization adjustments on behalf of caregivers and manufacturers. In one example, each time a mobile device is "synched" to a computer 54, such data may be transferred to various individuals as set forth in software options editable by the user of computer 54.

Photography Alternatives

While alluded to above, it is worth mentioning that the software may allow users to take photos and add them to schedules, countdowns, and choices directly, or the user may store the image for later use. Storage options may allow the user to select a category within the library in which to store the image, allow the user to make a new category, provide a default "custom images" or "other images" category or the like. Note that the user may be allowed to make new categories from old or stock images so as to have the images available to the user in a more intuitive format for that particular user. Additionally, photographs may need to be formatted to fit within the display area allocated to images by the software (e.g., images may need to be in a 4:3 landscape format). When a user is taking a photograph, a pop up reminder may alert the user that photographs need to be taken in a certain orientation (e.g., horizontally) to be used without modification by the software of the present disclosure. Alternatively, pictures with the wrong aspect ratio may be modified to fit (e.g., letter-box style black bars used to pad the photograph to fit).

Sharing Schedule

As a permutation on a schedule, a feature may be used which lets a user select pictures or images of two people and another image of an object being passed between the two people to simulate sharing the object. For example, if a toy is to be given to a first person and then shared with a second person, a picture of each person is added along with a picture of the toy. The mobile terminal 10 shows the picture of the toy proximate the picture of the first person and perhaps a countdown and then shows the picture of the toy proximate the picture of the second person. In another example, a scroll command of the IPHONE™ may be used to "slide" an image from one area of display 16 to another area in hopes of demonstrating or encouraging sharing behavior. For example, when rotated on its side, the left side of display 16 may show a picture of "Jimmy" while the right side shows a picture of "Sally". A "pinwheel" icon is also shown, and may be dragged, slid, or otherwise moved from one side of the screen to another. That is, by sliding the pinwheel from the left to the right side of the screen, a caregiver demonstrates to Jimmy that he should share his pinwheel with Sally.

RULES OF INTERPRETATION & GENERAL DEFINITIONS

Numerous embodiments are described in this disclosure, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features of the invention that must be present in all embodiments.

Neither the Title (set forth at the beginning of the first page of this disclosure) nor the Abstract (set forth at the end of this disclosure) is to be taken as limiting in any way as the scope of the disclosed invention(s).

The term "product" means any machine, manufacture and/or composition of matter as contemplated by 35 U.S.C. §101, unless expressly specified otherwise.

The terms "an embodiment", "embodiment", "embodiments", "the embodiment", "the embodiments", "one or more embodiments", "some embodiments", "one embodiment" and the like mean "one or more (but not all) disclosed embodiments", unless expressly specified otherwise.

The terms "the invention" and "the present invention" and the like mean "one or more embodiments of the present invention."

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "plurality" means "two or more", unless expressly specified otherwise.

The term "herein" means "in the present disclosure, including anything which may be incorporated by reference", unless expressly specified otherwise.

The phrase "at least one of", when such phrase modifies a plurality of things (such as an enumerated list of things) means any combination of one or more of those things, unless expressly specified otherwise. For example, the phrase at least one of a widget, a car and a wheel means either (i) a widget, (ii) a car, (iii) a wheel, (iv) a widget and a car, (v) a widget and a wheel, (vi) a car and a wheel, or (vii) a widget, a car and a wheel.

The phrase "based on" does not mean "based only on", unless expressly specified otherwise. In other words, the phrase "based on" describes both "based only on" and "based at least on".

Where a limitation of a first claim would cover one of a feature as well as more than one of a feature (e.g., a limitation such as "at least one widget" covers one widget as well as more than one widget), and where in a second claim that depends on the first claim, the second claim uses a definite article "the" to refer to the limitation (e.g., "the widget"), this does not imply that the first claim covers only one of the feature, and this does not imply that the second claim covers only one of the feature (e.g., "the widget" can cover both one widget and more than one widget).

Each process (whether called a method, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device or article is described herein, more than one device or article (whether or not they cooperate) may alternatively be used in place of the single device or article that is described. Accordingly, the functionality that is described as being possessed by a device may alternatively be possessed by more than one device or article (whether or not they cooperate).

Similarly, where more than one device or article is described herein (whether or not they cooperate), a single device or article may alternatively be used in place of the more than one device or article that is described. For example, a plurality of computer-based devices may be substituted with a single computer-based device. Accordingly, the various functionality that is described as being possessed by more than one device or article may alternatively be possessed by a single device or article.

The functionality and/or the features of a single device that is described may be alternatively embodied by one or more other devices that are described but are not explicitly described as having such functionality and/or features. Thus, other embodiments need not include the described device itself, but rather can include the one or more other devices which would, in those other embodiments, have such functionality/features.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

Headings of sections provided in this disclosure are for convenience only, and are not to be taken as limiting the disclosure in any way.

"Determining" something can be performed in a variety of manners and therefore the term "determining" (and like terms) includes calculating, computing, deriving, looking up (e.g., in a table, database or data structure), ascertaining, recognizing, and the like.

A "display" as that term is used herein is an area that conveys information to a viewer. The information may be dynamic, in which case, an LCD, LED, CRT, LDP, rear projection, front projection, or the like may be used to form the display. The aspect ratio of the display may be 4:3, 16:9, or the like. Furthermore, the resolution of the display may be any appropriate resolution such as 480i, 480p, 720p, 1080i, 1080p or the like. The format of information sent to the display may be any appropriate format such as standard definition (SDTV), enhanced definition (EDTV), high definition (HD), or the like. The information may likewise be static, in which case, painted glass may be used to form the display. Note that static information may be presented on a display capable of displaying dynamic information if desired.

The present disclosure frequently refers to a "control system". A control system, as that term is used herein, may be a computer processor coupled with an operating system, device drivers, and appropriate programs (collectively "software") with instructions to provide the functionality described for the control system. The software is stored in an associated memory device (sometimes referred to as a computer readable medium). While it is contemplated that an appropriately programmed general purpose computer or computing device may be used, it is also contemplated that hard-wired circuitry or custom hardware (e.g., an application specific integrated circuit (ASIC)) may be used in place of, or in combination with, software instructions for implementation of the processes of various embodiments. Thus, embodiments are not limited to any specific combination of hardware and software.

A "processor" means any one or more microprocessors, CPU devices, computing devices, microcontrollers, digital signal processors, or like devices. Exemplary processors are the INTEL PENTIUM or AMD ATHLON processors.

The term "computer-readable medium" refers to any medium that participates in providing data (e.g., instructions) that may be read by a computer, a processor or a like device. Such a medium may take many forms, including but not limited to, non-volatile media, volatile media, and transmission media. Non-volatile media include, for example, optical or magnetic disks and other persistent memory. Volatile media include DRAM, which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during RF and IR data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, a USB memory stick, a dongle, any other memory chip or cartridge, a carrier wave, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols. For a more exhaustive list of protocols, the term "network" is defined below and includes many exemplary protocols that are also applicable here.

It will be readily apparent that the various methods and algorithms described herein may be implemented by a control system and/or the instructions of the software may be designed to carry out the processes of the present invention.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models, hierarchical electronic file structures, and/or distributed databases) could be used to store and manipulate the data types described herein. Likewise, object methods or behaviors of a database can be used to implement various processes, such as those described herein. In addition, the databases may, in a known manner, be stored locally or remotely from a device that accesses data in such a database. Furthermore, while unified databases may be contemplated, it is also possible that the databases may be distributed and/or duplicated amongst a variety of devices.

As used herein a "network" is an environment wherein one or more computing devices may communicate with one another. Such devices may communicate directly or indirectly, via a wired or wireless medium such as the Internet, Local Area Network (LAN), Wide Area Network (WAN), or Ethernet (or IEEE 802.3), Token Ring, or via any appropriate communications means or combination of communications means. Exemplary protocols include but are not limited to: BLUETOOTH™, TDMA, CDMA, GSM, EDGE, GPRS, WCDMA, AMPS, D-AMPS, IEEE 802.11 (WI-FI), IEEE 802.3, TCP/IP, or the like. Note that if video signals or large files are being sent over the network, a broadband network may be used to alleviate delays associated with the transfer of such large files, however, such is not strictly required. Each of the devices is adapted to communicate on such a communication means. Any number and type of machines may be in communication via the network. Where the network is the Internet, communications over the Internet may be through a website maintained by a computer on a remote server or over an online data network including commercial online service providers, bulletin board systems, and the like. In yet other embodiments, the devices may communicate with one another over RF, cellular networks, cable TV, satellite links, and the like. Where appropriate encryption or other security measures such as logins and passwords may be provided to protect proprietary or confidential information.

Communication among computers and devices may be encrypted to insure privacy and prevent fraud in any of a variety of ways well known in the art. Appropriate cryptographic protocols for bolstering system security are described in Schneier, APPLIED CRYPTOGRAPHY, PROTOCOLS, ALGORITHMS, AND SOURCE CODE IN C, John Wiley & Sons, Inc. 2d ed., 1996, which is incorporated by reference in its entirety.

The present disclosure provides, to one of ordinary skill in the art, an enabling description of several embodiments and/or inventions. Some of these embodiments and/or inventions may not be claimed in the present disclosure, but may nevertheless be claimed in one or more continuing applications that claim the benefit of priority of the present disclosure.

What is claimed is:

1. A non-transitory computer readable medium comprising software adapted to operate with a mobile terminal having a vertical orientation having a longer axis extending from a top side to a bottom side and a horizontal orientation having the longer axis extending from a left side to a right side, the software with instructions to:
provide at least three functions to a first user, those functions including a graphical schedule creator, a graphical countdown timer, and a graphical choice selection;
interoperate with images from at least three image sources including a library of stock images, images taken by a camera associated with the mobile terminal, and images downloaded from a distributed network;
allow a first user to select one of the functions such that if the first user selects the countdown timer, the first user may:
select, from at least one of the at least three sources, a timer image associated with an activity to be performed by a second user;
allow the first user to set a duration of time for the activity to be performed by the second user and associate the timer with the timer image; and
activate the timer, thereby beginning a countdown animation to convey visually that time is elapsing and show the timer image with the timer to the second user;
if the first user selects the choice selection:
while the mobile terminal is in the vertical orientation, allow the first user to select two or more choice images from the at least three image sources for later presentation to a second user, wherein the first user is initially offered a choice as to which source to use for selecting each of the two or more choice images, and if the first user selects the library of stock images, providing a list of categories of images stored in the library of stock images; and
while the mobile terminal is in the horizontal orientation, allow the first user to present the two or more choice images to the second user; and
if the first user selects the graphical schedule creator:
while the mobile terminal is in the vertical orientation, allow the first user to create a graphical schedule by allowing the first user to select at least one image from one of the at least three image sources, and if the first user selects the library of stock images, present one or more categories of images;
receive a selection from the first user of one of the one or more categories of images; and
present one or more thematically-linked images associated with the selection from which the first user may make an image selection;
otherwise allow the first user to make a different image selection from a different image source;
save the graphical schedule for later presentation to a second user; and
display in the horizontal orientation for the second user the graphical schedule.

2. The computer readable medium of claim 1 wherein the instructions to display in the horizontal orientation for the second user in the graphical schedule comprise instructions that cause images within the graphical schedule to be enlarged in comparison to how images are presented in the vertical orientation.

3. The computer readable medium of claim 1 wherein the software is further adapted to interface with a microphone to capture audio for use with the countdown timer, choice selection, or graphical schedule.

4. The computer readable medium of claim 1 wherein the software is further adapted to interface with a video camera to capture video for use with the countdown timer, choice selection, or graphical schedule.

5. The computer readable medium of claim 1 wherein the countdown timer function displays a numeric indication of time remaining in an activity with the timer image and a countdown animation.

6. The computer readable medium of claim 1 wherein the instructions further comprise instructions to provide a reward to the second user based on completion of a graphical schedule.

7. The computer readable medium of claim 6 wherein the reward comprises a graphical indication of the reward.

8. The computer readable medium of claim 7 wherein the graphical indication is selected from a group consisting of: tokens, points, coins, and stars.

9. The computer readable medium of claim 6 wherein the reward comprises an indication of a tangible benefit that may be allocated to the second user outside the software.

10. The computer readable medium of claim 1 wherein the instructions allow the first user to edit categories of images.

11. The computer readable medium of claim 1 wherein the instructions allow navigation between the countdown timer, choice selection, and graphical schedule functions by selection of a tab indicative of a function.

12. The computer readable medium of claim 11 wherein the instructions allow the tabs to persist at a bottom of the display screen.

13. The computer readable medium of claim 1 wherein the software further comprises further instructions allowing the first user to drag and drop images within the graphical schedule so as to rearrange the images within the graphical schedule.

14. A mobile terminal comprising:
a housing comprising a longer axis and positionable in a vertical orientation with the longer axis extending from a top side to a bottom side and a horizontal orientation with the longer axis extending from a left side to a right side;
a wireless transceiver operative to work in a wireless communication network and configured to access a computer network;
memory for storing software and an image library;
a user interface comprising:
a display;
a microphone; and
a camera; and
a control system operatively coupled to the wireless transceiver and the user interface and adapted to:
provide at least three functions to a first user, those functions including a graphical schedule creator, a graphical countdown timer, and a graphical choice selection;
interoperate with images from at least three image sources including a library of stock images, images taken by a camera associated with the mobile terminal, and images downloaded from a distributed network;
allow a first user to select one of the functions such that if the first user selects the countdown timer, the first user may:
select, from at least one of the at least three sources, a timer image associated with an activity to be performed by a second user;
allow the first user to set a duration of time for the activity to be performed by the second user and associate the timer with the timer image; and
activate the timer, thereby beginning a countdown animation to convey visually that time is elapsing and show the timer image with the timer to the second user;
if the first user selects the choice selection:
while the mobile terminal is in the vertical orientation, allow the first user to select two or more choice images from the at least three image sources for later presentation to a second user, wherein the first user is initially offered a choice as to which source to use for selecting each of the two or more choice images, and if the first user selects the library of stock images, providing a list of categories of images stored in the library of stock images; and
while the mobile terminal is in the horizontal orientation, allow the first user to present the two or more choice images to the second user; and
if the first user selects the graphical schedule creator:
while the mobile terminal is in the vertical orientation, allow the first user to create a graphical schedule by allowing the first user to select at least one image from one of the at least three image sources, and if the first user selects the library of stock images, present one or more categories of images;
receive a selection from the first user of one of the one or more categories of images; and
present one or more thematically-linked images associated with the selection from which the first user may make an image selection;
otherwise allow the first user to make a different image selection from a different image source;
save the graphical schedule for later presentation to a second user; and
display in the horizontal orientation for the second user the graphical schedule.

15. The mobile terminal of claim 14 wherein the wireless transceiver is adapted to voice or text-based communications.

16. The mobile terminal of claim 14 wherein the camera is adapted to capture still and video images.

17. A method comprising:
providing at least three functions to a first user of a mobile terminal comprising a housing comprising a longer axis and positionable in a vertical orientation with the longer axis extending from a top side to a bottom side and a horizontal orientation with the longer axis extending from a left side to a right side, those functions including a graphical schedule creator, a graphical countdown timer, and a graphical choice selection;
providing images from at least three image sources including an image library, images taken by a camera associated with the mobile terminal, and downloaded from a distributed computer network;
allowing a first user to select one of the functions such that if the first user selects the countdown timer, the first user may:
select, from at least one of the at least three sources, a timer image associated with an activity to be performed by a second user;
allow the first user to set a duration of time for the activity to be performed by the second user and associate the timer with the timer image; and
activate the timer, thereby beginning a countdown animation to convey visually that time is elapsing and show the timer image with the timer to the second user;
if the first user selects the choice selection:
while the mobile terminal is in the vertical orientation, allow the first user to select two or more choice images from the at least three image sources for later presentation to a second user, wherein the first user is initially offered a choice as to which source to use for selecting each of the two or more choice images, and if the first user selects the library of stock images, providing a list of categories of images stored in the library of stock images; and
while the mobile terminal is in the horizontal orientation, allow the first user to present the two or more choice images to the second user; and if the first user selects the graphical schedule creator:
  while the mobile terminal is in the vertical orientation, allow the first user to create a graphical schedule by allowing the first user to select at least one image from one of the at least three image sources, and if the first user selects the library of stock images, present one or more categories of images;
  receive a selection from the first user of one of the one or more categories of images; and
  present one or more thematically-linked images associated with the selection from which the first user may make an image selection;
  otherwise allow the first user to make a different image selection from a different image source;
saving the graphical schedule for later presentation to a second user; and
displaying in the horizontal orientation for the second user the graphical schedule.

\* \* \* \* \*